United States Patent
Wang et al.

(10) Patent No.: US 12,303,806 B2
(45) Date of Patent: May 20, 2025

(54) APPARATUSES FOR PURIFICATION OF GEL DROPLETS SUPPORTING BIOLOGICAL TISSUE

(71) Applicant: Duke University, Durham, NC (US)

(72) Inventors: Zhaohui Wang, Durham, NC (US); Xiling Shen, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 18/126,393

(22) Filed: Mar. 25, 2023

(65) Prior Publication Data

US 2023/0364528 A1 Nov. 16, 2023

Related U.S. Application Data

(62) Division of application No. 17/233,950, filed on Apr. 19, 2021, now Pat. No. 11,628,382.

(60) Provisional application No. 63/070,334, filed on Aug. 26, 2020.

(51) Int. Cl.
| | | |
|---|---|---|
| *B01D 69/02* | (2006.01) | |
| *B01D 15/38* | (2006.01) | |
| *B01D 17/02* | (2006.01) | |
| *C12M 1/00* | (2006.01) | |
| *C12M 3/06* | (2006.01) | |

(52) U.S. Cl.
CPC ......... *B01D 17/0202* (2013.01); *B01D 69/02* (2013.01); *C12M 23/16* (2013.01); *C12M 29/04* (2013.01); *B01D 15/38* (2013.01); *B01D 2325/02834* (2022.08); *B01D 2325/38* (2013.01)

(58) Field of Classification Search
CPC ...... C12M 25/01; C12M 23/16; C12M 29/04; B01D 15/38; B01D 17/0202; B01D 17/085; B01D 69/02; B01D 2325/02834; B01D 2325/38
See application file for complete search history.

(56) References Cited

U.S. PATENT DOCUMENTS

| | | |
|---|---|---|
| 5,578,485 A | 11/1996 | Naughton et al. |
| 2016/0022873 A1 | 1/2016 | Besner et al. |
| 2018/0258403 A1 | 9/2018 | Lutolf et al. |
| 2019/0264199 A1 | 8/2019 | Williams et al. |

FOREIGN PATENT DOCUMENTS

| | | | |
|---|---|---|---|
| WO | WO-2016145242 A1 * | 9/2016 | ........... C12N 5/0012 |
| WO | 2019/010587 A1 | 1/2019 | |

OTHER PUBLICATIONS

Dolega et al. Controlled 3D culture in Matrigel microbeads to analyze clonal acinar development (Year: 2015).*
International Search Report and Written Opinion dated Feb. 8, 2022 in associated PCT Application No. PCT/ US21/47645 (13 pages).
International Search Report and Written Opinion dated Feb. 28, 2023 in associated PCT Application No. PCT/US21/047,634 (8 pages).
Extended European Search Report for European Patent Application No. 21862690.1 dated Dec. 16, 2024.
Langer, Krzysztof et al., "Rapid Production and Recovery of Cell Speroids by Automated Droplet Microfluidics", Society for Laboratory Automation and Screening, Apr. 1, 2020 (Apr. 1, 2020), pp. 111-122, XP055929995, UR:: https://www.sciencedirect.com/science/article/pii/S2472630322010263/pdfft?md5= 69225ee139714f84aad7acffac0fe013pid=1-s2.00S2472630320010263-main.pdf.
Office Action dated Jan. 19, 2025 for Chinese Patent Application No. 202180050185.5.
Langer, Krzysztof et al., Rapid Production and Recovery of Cell Spheroids by Automated Droplet Microfluidics, SLAS Technology 2020, vol. 25(2) 111-122.

* cited by examiner

*Primary Examiner* — Ryan B Huang
*Assistant Examiner* — Tak L Chiu
(74) *Attorney, Agent, or Firm* — Olive Law Group, PLLC

(57) ABSTRACT

Method and apparatuses for forming gel droplets including biological tissue (e.g., cells), and in particular, methods and apparatuses for removing oil from the gel droplets comprising dissociated cells (including micro-organospheres) are described herein. Although it is beneficial to use oil in the formation of these gel droplets, and particularly micro-organospheres, oil may inhibit growth and survival of the cells within the gel droplets. The methods and apparatuses described herein may permit the removal of oil and may enhance survival and quality of the resulting gel droplets.

21 Claims, 12 Drawing Sheets

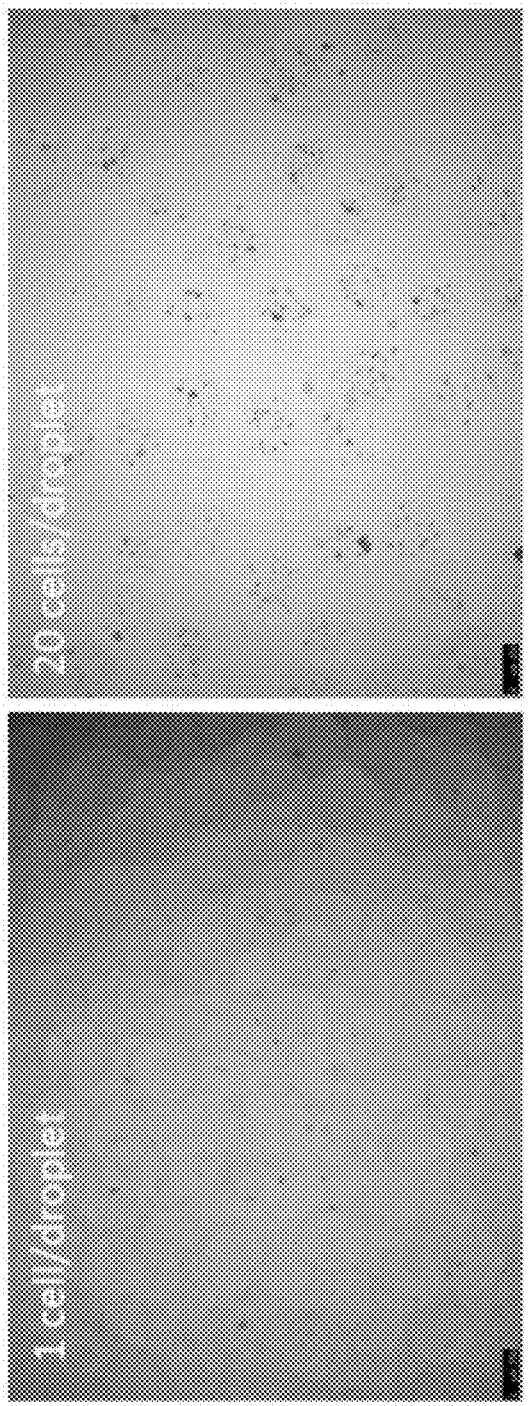
FIG. 8B
FIG. 8A
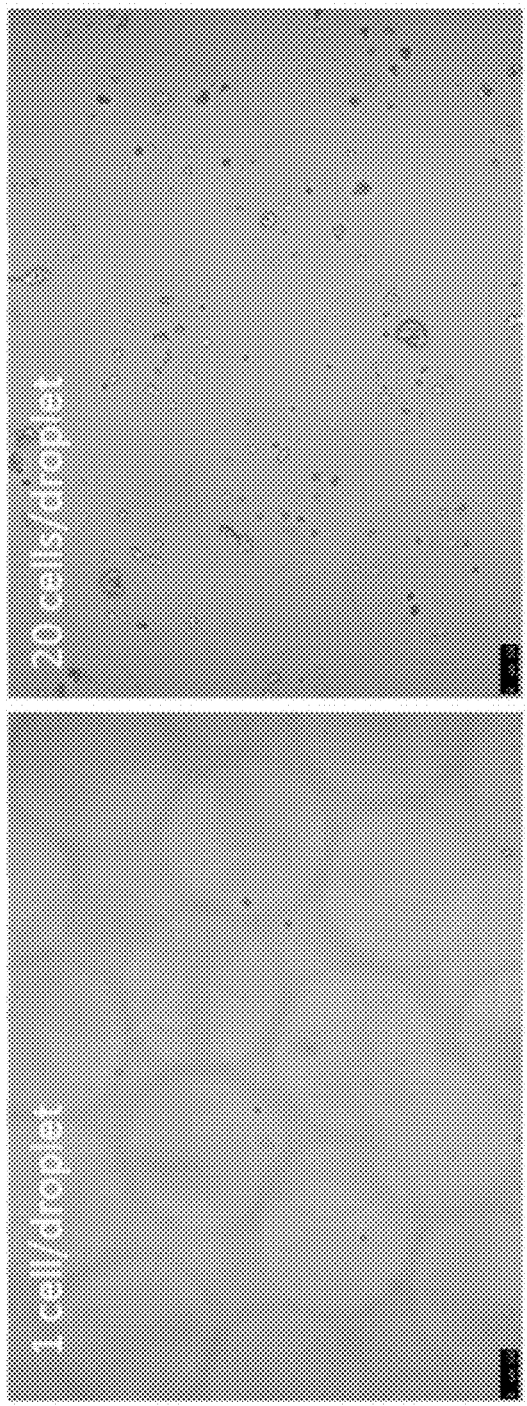
FIG. 8D
FIG. 8C

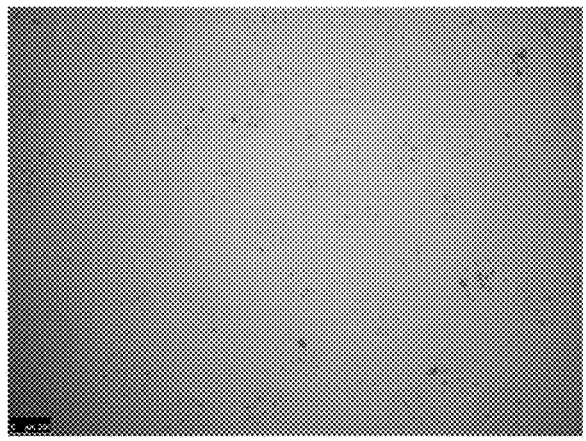 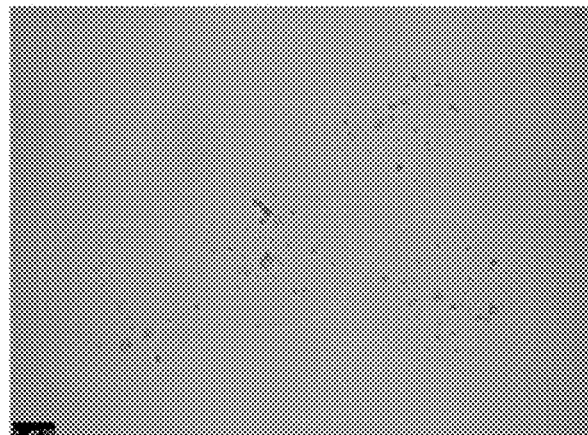
FIG. 18A  FIG. 18B
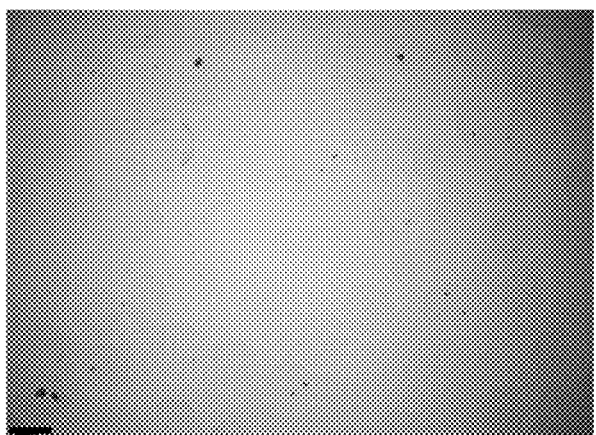 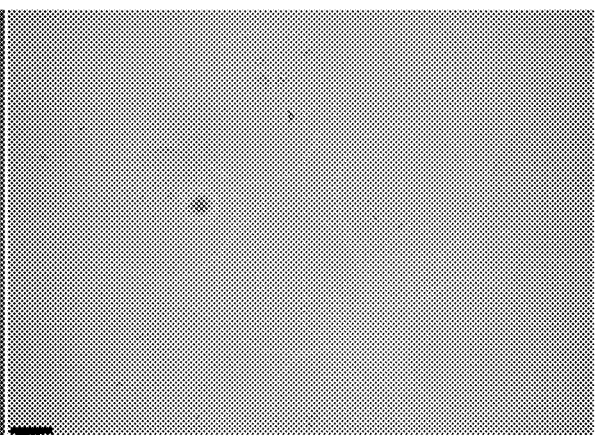
FIG. 19A  FIG. 19B
 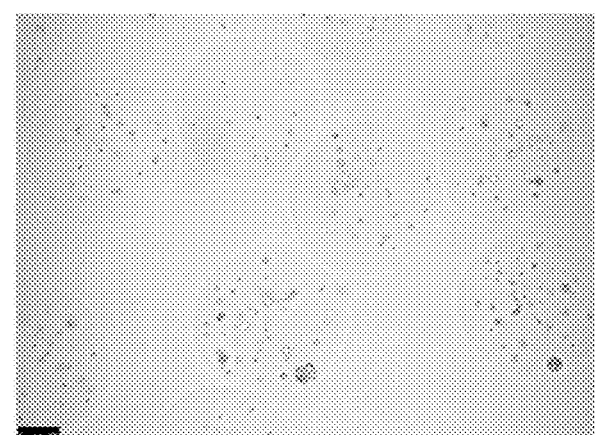
FIG. 20A  FIG. 20B

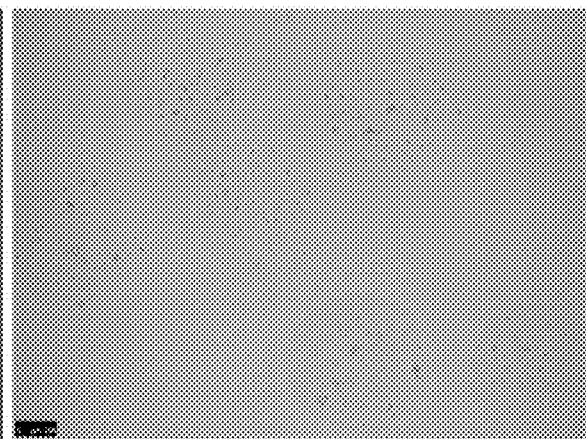
FIG. 21A　　　　　　　　　　FIG. 21B
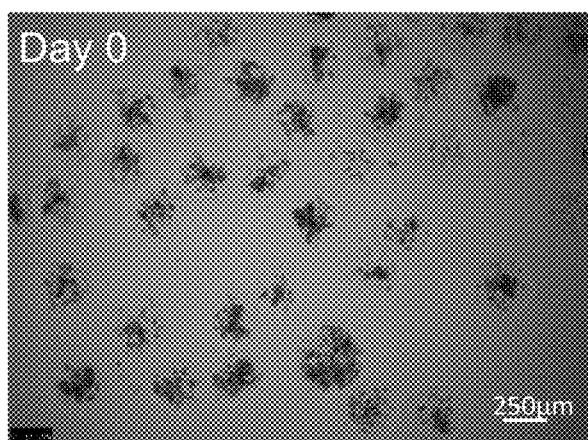
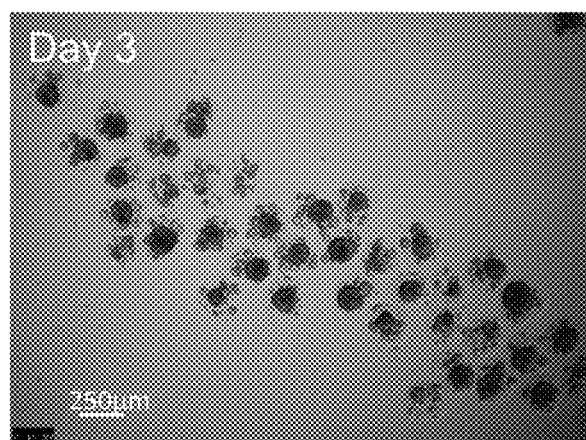
FIG. 22A　　　　　　　　　　FIG. 22B
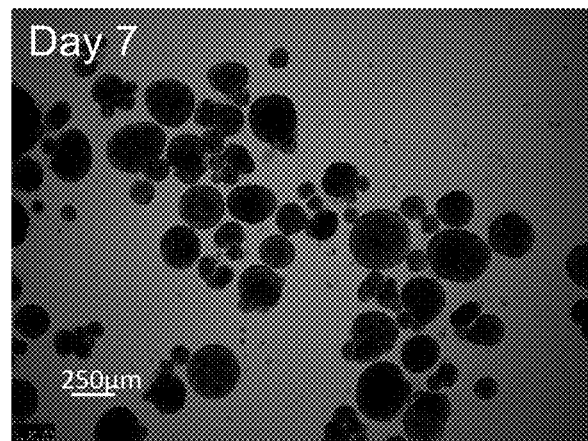
FIG. 22C

APPARATUSES FOR PURIFICATION OF GEL DROPLETS SUPPORTING BIOLOGICAL TISSUE

CROSS REFERENCE TO RELATED APPLICATION

This divisional application claims priority to U.S. nonprovisional patent application Ser. No. 17/233,950, filed Apr. 19, 2021, and titled "METHODS AND APPARATUSES FOR PURIFICATION OF GEL DROPLETS SUPPORTING BIOLOGICAL TISSUE", which claims priority to U.S. provisional patent application No. 63/070,334, filed Aug. 26, 2020, titled "METHODS AND APPARATUSES FOR PURIFICATION OF GEL DROPLETS SUPPORTING BIOLOGICAL TISSUE"; the disclosures of which are herein incorporated by reference in their entireties.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The methods and apparatuses described herein relate to method and apparatuses for forming gel droplets including biological tissue (e.g., organospheres, e.g., micro-organospheres, organoids, micro-organoids, etc.). Specifically, described herein are methods and apparatuses for forming these gel droplets including removing oil which may otherwise inhibit or harm the cells within the gel droplets.

BACKGROUND

Model cell and tissue systems are useful for biological and medical research. The most common practice is to derive immortalized cell lines from tissue and culture them in two-dimensional (2D) conditions (e.g., in Petri dish or well plate). However, although immensely useful for basic research, 2D cell lines do not correlate well with individual patient response to therapy. In particular, three-dimensional cell culture models are proving particularly helpful in developmental biology, disease pathology, regenerative medicine, drug toxicity and efficacy testing, and personalized medicine. For example, spheroids and organoids are three-dimensional cell aggregates that have been studied.

Multicellular tumor spheroids were first described in the early 70s and obtained by culture of cancer cell lines under non-adherent conditions. Spheroids are typically formed from cancer cell lines as freely floating cell aggregates in ultra-low attachment plates. Spheroids have been shown to maintain more stem cell associated properties than 2D cell culture.

Organoids are in-vitro derived cell aggregates that include a population of stem cells that can differentiate into cell of major cell lineages. Organoids typically have a diameter of more than one mm diameter, and are cultured through passages. It is typically slower to grow and expand organoid culture than 2D cell culture.

Recently, micro-organoids have been developed, which may be used for rapid and reliable screening, particularly for personalized medicine, such as performing ex-vivo testing of drug response. Micro-organoids may be smaller, more homogenous is shape and cell number, and may include a smaller number of cells than traditional organoids or tumor spheroids.

However, all of these types of organoids (traditional organoids, spheroids and micro-organospheres), which may be referred to herein as "organospheres," for convenience, are all typically formed using oil. For example, organoids may be formed by mixing an unpolymerized matrix material (e.g., a substrate basement membrane matrix such as MATRIGEL) with dissociated tissue, such as tumor tissue, and then polymerizing this mixture into spheres within a stream or bath of immiscible carrier fluid, such as an oil. Although the oil is helpful for forming the spheres, the oil may inhibit the growth of the cells within the organospheres. The oil may be washed by repeated rinses, however such rinses are not very effective at removing all of the oil, and may also require longer time periods, during which the cells remain exposed to the oil.

An emulsification destabilization agent, such as perfluoro octanol (PFO) has been used to remove oil from organospheres. PFO may also disrupt the growth and viability of the cells within the organospheres. What is needed are methods and apparatuses for removal of oil from organospheres, including in particular from micro-organospheres. The methods and apparatuses described herein may address this need.

SUMMARY OF THE DISCLOSURE

Described herein method and apparatuses of forming gel droplets containing biological tissue. In particular, described herein are methods and apparatuses for removing oil from gel droplets shortly or immediately after they form. The methods and apparatuses described herein may use a membrane-based demulsification, e.g., using a hydrophobic membrane to remove the oil from the gel droplets. These methods and apparatuses may very rapidly and effectively remove oil (e.g., over 99% of the oil on or around the gel droplets). These methods and apparatuses may be performed without the use of chemical demulsification agents (e.g., perfluoro octanol, PFO), and therefore may have substantially lower toxicity to cells within the gel droplets. These methods and apparatuses have been shown to provide gel droplets with viable biological tissue have an exceptionally high recovery rate (with less than 5% loss of the gel droplets) and may be automated. The resulting gel droplets may be cultured and/or used immediately or after culturing for performing one or more assays, including screening, drug toxicity, etc., assays.

In general, the methods and apparatuses described herein may include the formation of gel droplets including biological tissue. These gel droplets may be referred to herein as organospheres, and may include (but are not limited to) any gel droplet that may be formed with or in oil, such as in particular micro-organospheres, micro-organoids, microspheroids, and in some cases organoids and/or spheroids. Any of the gel droplets supporting biological tissue (e.g., dissociated cells) described herein may contain cells originating from a patient and/or tissue culture. For example, the cells may be extracted from a small patient biopsy, (e.g., for quick diagnostics to guide therapy), from resected patient tissue, including resected primary tumor or part of a dysfunctional organ (e.g., for high-throughput screening), and/ or from already established PDMCs, including patient-derived xenografts (PDX). These gel droplets may be formed from primary cells that are normal (e.g., normal organ tissue) or from tumor tissue. For example, in some variations, these methods and apparatuses may form gel droplets from cancerous tumor biopsy tissue, enabling tailored treatments that can selected using the particular tumor tissue examined.

The gel droplets may be, but are not limited to, micro-organospheres. For example, dissociated primary cells from the patient biopsy may be combined with a fluid matrix material, such as a substrate basement membrane matrix (e.g., MATRIGEL), to form and gel droplets, such as a micro-organospheres. Micro-organospheres may have a pre-defined range of sizes (such as diameters, e.g., between 10 µm and 700 µm and any sub-range therewithin), and initial number of primary cells (e.g., between 1 and 1000, and in particular lower numbers of cells, such as between 1-200). The number of cells and/or the diameter may be controlled within, e.g., +/−5%, 10%, 15%, 20%, 25%, 30%, etc. These micro-organospheres, when formed as described herein, may be stable for use and testing within a very short period of time, including within minutes, hours, or days after being formed, particularly because they may be free of oil and/or demulsifying agent (e.g., PFO). This may allow for rapid testing. The gel droplets described herein may more robustly form 3D cellular structures that replicate and correspond to the tissue environment from which they were taken, such as a three-dimensional (3D) tumor microenvironment.

In particular, described herein are methods processing gel droplets including biological tissue (e.g., cells), such as methods of processing organospheres or micro-organospheres. Any of these methods may include: forming a plurality of gel droplets in an oil, wherein the gel droplets comprise cells from a dissociated tissue sample distributed within a polymerized sphere of matrix material, the gel droplets having the cells distributed therein; and contacting the gel droplets against a hydrophobic membrane so that the oil is removed from the gel droplets through or into the hydrophobic membrane.

The gel droplets may comprise micro-organospheres having a diameter of between 50-500 µm. Any of these methods may include removing at least 99% of the oil from the gel droplets when contacting the gel droplets against a hydrophobic membrane.

For example, contacting the gel droplets against a hydrophobic membrane may include passing the gel droplets through a chamber (e.g., tube, channel, etc.) at least partially formed by the hydrophobic membrane. The chamber may comprise a tunnel or tube formed by the hydrophobic membrane. In any of these methods, negative pressure (e.g., vacuum may optionally be applied on one side of the membrane, and/or the solution including the gel droplets may be driven against the membrane. Alternatively, in any of these variations the gel droplets may simply be contacted to the hydrophobic membrane, without requiring the application of force, including by applying negative pressure.

For example in some variations, contacting the gel droplets against a hydrophobic membrane comprises eluting the gel droplets into a funnel formed by the hydrophobic membrane. Contacting the gel droplets against a hydrophobic membrane may comprise filtering the gel droplets against the hydrophobic membrane. In general, contacting the gel droplets against a hydrophobic membrane may comprise passing a solution including the gel droplets over the hydrophobic membrane.

Any appropriate porous hydrophobic surface, including but not limited to a hydrophobic "membrane" may be used. For example the hydrophobic surface (e.g., membrane) may have a pore size that is between 0.1 and 5 µm (e.g., between about 0.1 and 2 µm, between about 0.2 and 4 µm, between about 0.1 and 1 µm, between about 0.3 and 3 µm, etc.). The surface texture of the porous hydrophobic surface may be rough rather than smooth.

In general, contacting the gel droplets against a hydrophobic membrane may comprises retaining the gel droplets in an aqueous medium. For example, the gel droplets may be retained with an aqueous buffer/media on one side of the porous hydrophobic surface while the oil is wicked or removed into or through the porous hydrophobic surface.

As mentioned above, any of the methods and apparatuses for forming and/or processing gel droplets described herein may be used for organoids, spheroids or micro-organospheres. For example, in some variations the gel droplets may each comprises between 1 and 200 of the cells distributed therein.

Any of these methods may include washing the gel droplets on the hydrophobic membrane with an aqueous medium. The gel droplets (e.g., the microorganospheres) may be washed by adding an aqueous solution (e.g. buffer, such as PBS, culture media, etc.) over the membrane, or adding additional aqueous solution to the droplets and re-exposing them to the hydrophobic membrane. In some examples, the droplets may be combined with an aqueous solution to rinse before contacting the droplets against the hydrophobic membrane, then rinsing while on the hydrophobic membrane with additional aqueous solution. Alternatively or additionally, aqueous solution may be added to the droplets and they may be again exposed to the hydrophobic membrane (or a new hydrophobic membrane, or new region of the same hydrophobic membrane). In some example, multiple rinses/washes and contact with one or more hydrophobic membranes may be performed. In such cases, hydrophobic membranes having different properties may be used. The method may include culturing the organizers in a culture medium.

For example, a method of processing gel droplets may include: forming a plurality of gel droplets in an oil, wherein the gel droplets comprise cells from a dissociated tissue sample distributed within a sphere of matrix material, the gel droplets having a diameter of between 50 and 500 µm with between 1 and 200 of the cells distributed therein; and contacting the gel droplets against a hydrophobic membrane so that at least 98% of the oil is removed from the gel droplets on or into the hydrophobic membrane; washing the gel droplets on the hydrophobic membrane with an aqueous medium; and culturing the organizers in a culture medium.

Any of the method described herein may include combining a dissociated primary tissue cells (including, but not limited to cancer/abnormal tissue, normal tissue, etc.) with a liquid matrix material to form an unpolymerized material, and then polymerizing the unpolymerized material to form gel droplets (e.g., micro-organospheres) within an oil or oil emulsion; these methods may then use a hydrophobic surface or membrane to remove the oil from the gel droplets.

Also described herein are apparatuses configured to perform any of these methods. For example, described herein are apparatuses for forming gel droplets, the apparatus comprising: a fluidic processor comprising a plurality of channels, including: a first channel configured to receive a dissociated tissue sample comprising dissociated cells and an unpolymerized matrix material, and a second channel configured to receive an oil and to intersect with the first channel to form polymerized gel droplets suspended in the oil; a demulsifying portion comprising a hydrophobic membrane in fluid communication with the fluidic processor and configured to remove oil from the gel droplets; and an elution channel configured to elute the gel droplets from the demulsifying portion using an aqueous solution.

When the gel droplets are micro-organospheres, the micro-organospheres may have diameters that are typically less than about 1000 µm (e.g., less than about 900 µm, less than about 800 µm, less than about 700 µm, less than about 600 µm, and in particular, less than about 500 µm) in diameter in which the dissociated primary tissue cells are distributed. In any of these gel droplets, the number of dissociated cells may be within a predetermined range, as mentioned above (e.g., between about 1 and about 500 cells, between about 1-200 cells, between about 1-150 cells, between about 100 cells, between about 1-75 cells, between about 1-50 cells, between about 1-30 cells, between about 1-20 cells, between about 1-10 cells, between about 5-15 cells, between about 20-30 cells, between about 30-50 cells, between about 40-60 cells, between about 50-70 cell, between about 60-80 cells, between about 70-90 cells, between about 80-100 cells, between about 90-110 cells, etc., including about 1 cell, about 10 cells, about 20 cells, about 30 cells, about 40 cells, about 50 cells, about 60 cells, about 70 cells, etc.). Any of these methods may be configured as described herein to produce gel droplets of repeatable size (e.g., having a narrow distribution of sizes).

The dissociated cells may be freshly biopsied and may be dissociated in any appropriate manner, including mechanical and/or chemical dissociation (e.g., enzymatic disaggregation by using one or more enzymes, such as collagenase, trypsin, etc.). The dissociated cells may optionally be treated, selected and/or modified. For example, the cells may be sorted or selected to identify and/or isolate cells having one or more characteristics (e.g., size, morphology, etc.). The cells may be marked (e.g., with one or more markers) that may be used to aid in selection. In some variations the cells may be sorted by a known cell-sorting technology, including but not limited to microfluidic cell sorting, fluorescent activated cell sorting, magnetic activated cell sorting, etc. Alternatively, the cells may be used without sorting.

In some variations, the dissociated cells may be modified by treatment with one or more agents. For example the cells may be genetically modified. In some variations the cells may be modified using CRISPR-Cas9 or other genetic editing techniques. In some variations the cells may be transfected by any appropriate method (e.g., electroporation, cell squeezing, nanoparticle injection, magnetofection, chemical transfection, viral transfection, etc.), including transfection with of plasmids, RNA, siRNA, etc. Alternatively, the cells may be used without modification.

One or more additional materials may be combined with the dissociated cells and fluid (e.g., liquid) matrix material to form the unpolymerized mixture. For example, the unpolymerized mixture may include additional cell or tissue types, including support cells. The additional cells or tissue may originate from different biopsy (e.g., primary cells from a different dissociated tissue) and/or cultured cells. The additional cells may be, for example immune cells, stromal cells, endothelial cells, etc. The additional materials may include medium (e.g., growth medium, freezing medium, etc.), growth factors, support network molecules (e.g., collagen, glycoproteins, extracellular matrix, etc.), or the like. In some variations the additional materials may include a drug composition. In some variations the unpolymerized mixture includes only the dissociated tissue sample (e.g., primary cells) and the fluid matrix material.

For example, in some variations, these methods may be performed by combing an unpolymerized matrix mixture with oil (e.g., liquid material) that is immiscible with the unpolymerized material. The method and apparatus may control the size and/or cell density of the gel droplets by, at least in part, controlling the flow of one or more of the unpolymerized matrix mixture (e.g., the dissociated tissue and fluid matrix) and the oil with the unpolymerized mixture. Following polymerization, typically within the oil, the gel droplets may be washed (e.g., in an aqueous medium, such as a buffered saline (e.g., phosphate buffered saline) and/or in cell culture medium) to remove some of the oil, and/or the gel droplets may be exposed to a porous hydrophobic surface, such as in particular a surface of a hydrophobic membrane. The oil may be removed from the gel droplets through or into the porous hydrophobic surface (e.g., into or through a hydrophobic membrane). The gel droplets may be separated or removed from the hydrophobic surface by rinsing, washing, flushing, etc. with a buffered solution and/or media.

In some variations, these methods may be performed using a microfluidics apparatus. In some variations, multiple gel droplets (e.g., micro-organospheres) may be formed in an oil using one or more microfluidic chambers and/or channels, including flow channels. A chamber, channel or other portion may be configured to remove oil from the gel droplets. For example, an oil-removing portion may include a channel or chamber including a porous hydrophobic surface (e.g. membrane) onto which the gel droplets may be placed into contact, including by flowing against the hydrophobic surface. The gel droplets may be driven (e.g., flowed) against the hydrophobic surface and/or allowed to rest against the hydrophobic surface for some period of time (e.g., x seconds or minutes, such as 1 second, 2 seconds, 3 seconds, 5 seconds, 10 seconds, 30 seconds, 60 seconds, 120 seconds, 3 minutes, 4 minutes, 5 minutes, etc.). The same apparatus may include multiple parallel channels, including parallel channels for removing oil.

Once the oil has been removed from the gel droplets, the gel droplets may be used immediately, and/or may be stored (e.g., frozen) and/or may be allowed to grow, e.g., by culturing. The gel droplets may be assayed either before or after culturing and/or may be cryopreserved either before or after culturing. The gel droplets may be cultured for any appropriate length of time, but in particular, may be cultured for between 1 day and 10 days (e.g., between 1 day and 9 days, between 1 day and 8 days, between 1 day and 7 days, between 1 day and 6 days, between 3 days and 9 days, between 3 days and 8 days, between 3 days and 7 days, etc.). The resulting gel droplets may be essentially free of oil and/or free of a demulsifying agent, such as PFO.

The matrix material may be a synthetic or non-synthetic unpolymerized basement membrane material. In some variations the unpolymerized basement material may comprise a polymeric hydrogel. In some variations the fluid matrix material may comprise a MATRIGEL. Thus, combining the dissociated tissue sample and the fluid matrix material may comprise combining the dissociated tissue sample with a basement membrane matrix. The tissue sample may be combined with the fluid matrix material within six hours of removing the tissue sample from the patient or sooner (e.g., within about 5 hours, within about 4 hours, within about 3 hours, within about 2 hours, within about 1 hour, etc.).

In any of the methods and apparatuses described herein, rather than, or in addition to, a hydrophobic membrane, a hydrophobic material (beads, surfaces, etc.) may be used to remove the oil. For example, the droplets (e.g., microorganospheres) may be contacted by a surface coated with a hydrophobic material to remove oil, and/or a camber including beads formed of a hydrophobic material.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

In FIG. 6, two separate techniques and structures for using a porous hydrophobic surface are illustrated (e.g., a funnel and a tube).

FIGS. 8A-8D illustrate examples of freshly formed gel droplets (e.g., micro-organospheres in this example) recovered following the use of a hydrophobic membrane to demulsify the gel droplets. FIG. 8A shows a view of a plurality of 1 cell/droplet gel droplets at low magnification (4×) objective. FIG. 8B shows a view of a plurality of 20 cell/droplet gel droplets at low magnification (4×) objective. FIG. 8C shows a higher (e.g., 10×) magnification view of gel droplets having 1 cell/droplet from which oil was removed using a hydrophobic membrane. FIG. 8D shows a higher (e.g., 10×) magnification view of gel droplets having 20 cells/droplet following removing of the oil as described herein.

FIGS. 18A-18B show examples of gel droplets formed from CRC19187 cells having 20 cells/droplet at 4× (FIG. 18A) or 10× (FIG. 18B) magnification, respectively.

FIGS. 19A-19B show examples of gel droplets formed from CRC19245 cells having 20 cell/droplet (FIG. 19A) at 4× or 10× (FIG. 19B) magnification, respectively.

FIGS. 20A-20B show examples of gel droplets formed from VERO cells having 1 cell/droplet (FIG. 20A) or 20 cells/droplet (FIG. 20B) at 4× or 10× magnification, respectively.

FIGS. 21A-21B show examples of gel droplets formed from mouse intestine organoids having 20 cell/droplet (FIG. 21A) or 20 cells/droplet (FIG. 21B) at 4× or 10× magnification, respectively.

FIGS. 22A-22C illustrate examples of micro-organospheres formed as described herein, from induced pluripotent stem cells (iPSCs) using the methods described herein. FIG. 22A shows the droplets (micro-organospheres) shortly after forming, following removal of the oil as described herein. FIG. 22B shows the micro-organospheres three days after forming. FIG. 22C shows the iPSC micro-organospheres at seven days.

FIG. 23A shows a sample of tissue that may be used as described herein to form the micro-organospheres; in FIG. 23A the tissue is olfactory tissue. FIG. 23B shows an example of a micro-organosphere formed from the tissue shown in FIG. 23A. FIG. 23C shows examples of micro-organospheres formed using distal lung tissue. FIG. 23D shows examples of micro-organospheres formed using tracheal tissue. FIG. 23E shows examples of micro-organospheres formed using proximal lung tissue. FIG. 23F shows examples of micro-organospheres formed using sinonasal mucosa.

Figure 1:
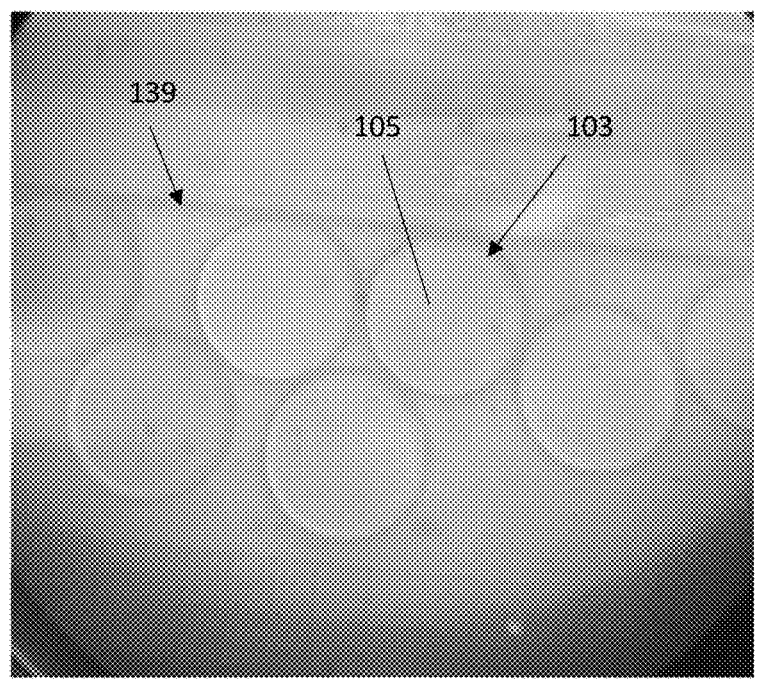
FIG. 1 shows one example of an image showing a plurality of gel droplets (in this example, patient-derived micro-organospheres) shortly after polymerizing, suspended within a channel containing the oil.

23K have been cultured for between 7-20 days following formation and removal of oil, as described herein.

DETAILED DESCRIPTION

In general, described herein are method and apparatuses for making gel droplets, including, for example, the micro-organospheres, that comprises a step and/or structure configured to remove oil from the gel droplets by using a porous surface.

The gel droplets described herein may typically be spheres formed from dissociated primary cells distributed within the base material. These gel droplets may be configured as micro-organospheres having a diameter of, e.g., between about 50 μm and about 500 μm (e.g., between about 50 μm and about 400 μm, about 50 μm and about 300 μm, about 50 μm and about 250 μm, etc.), and may contain between about 1 and 1000 dissociated primary cells distributed within the base material (e.g., between about 1 and 750, between about 1 and 500, between about 1 and 400, between about 1 and 300, between about 1 and 200, between about 1 and 150, between about 1 and 100, between about 1 and 75, between about 1 and 50, between about 1 and 40, between about 1 and 30, between about 1 and 20, etc.).

The removal of oil using a hydrophobic surface, such as but not limited to a hydrophobic membrane, may provide gel droplets that may be used immediately or cultured for a very brief period of time (e.g., 14 days or less, 10 days or less, 7 days or less, 5 days or less, etc.) and may allow the cells within the gel droplets to survive while maintaining much, if not all, of the characteristics of the tissue, including tumor tissue, from which they were extracted. When using a porous hydrophobic surface (such as a membrane) to remove oil from the gel droplets, the survival rate of the cells within the gel droplets is remarkably high, and the gel droplets may be cultured for days (or weeks) through multiple passages, in which the cells will divide, cluster and form structures similar to the parent tissue.

The gel droplets (e.g., droplet formed Micro-Organospheres) described herein may be formed, e.g., from patient-derived tumor samples that have been dissociated and suspended in a basement matrix (e.g., MATRIGEL). The gel droplets can be patterned onto a microfluidic microwell array, to be incubated, and dosed with drug compounds. This miniaturized assay maximizes the use of tumor samples and enables more drug compounds to be screened from a core biopsy at much lower cost per sample.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

The term "an unpolymerized mixture" is used herein to refer to a composition comprising biologically-relevant materials, including a dissociated tissue sample and a first fluid matrix material. The fluid matrix material is typically a material that may be polymerized to form a support or support network for the dissociated tissue (cells) dispersed within it. Once polymerized, the polymerized material may form a hydrogel and may be formed or and/or may include proteins forming the biocompatible medium, in addition to the cells. A suitable biocompatible medium for use in accordance with the presently-disclosed subject matter can typically be formed from any biocompatible material that is a gel, a semi-solid, or a liquid, such as a low-viscosity liquid, at room temperature (e.g., 25° C.) and can be used as a three-dimensional substrate for cells, tissues, proteins, and other biological materials of interest. Exemplary materials that can be used to form a biocompatible medium in accordance with the presently-disclosed subject matter include, but are not limited to, polymers and hydrogels comprising collagen, fibrin, chitosan, MATRIGEL™ (BD Biosciences, San Jose, Calif), polyethylene glycol, dextrans including chemically crosslinkable or photo-crosslinkable dextrans, and the like, as well as electrospun biological, synthetic, or biological-synthetic blends. In some embodiments, the biocompatible medium is comprised of a hydrogel.

The term "hydrogel" is used herein to refer to two- or multi-component gels comprising a three-dimensional network of polymer chains, where water acts as the dispersion medium and fills the space between the polymer chains. Hydrogels used in accordance with the presently-disclosed subject matter are generally chosen for a particular application based on the intended use of the structure, taking into account the parameters that are to be used to form the gel droplets, as well as the effect the selected hydrogel will have on the behavior and activity of the biological materials (e.g., cells) incorporated into the biological suspensions that are to be placed in the structure. Exemplary hydrogels of the presently-disclosed subject matter can be comprised of polymeric materials including, but not limited to: alginate, collagen (including collagen types I and VI), elastin, keratin, fibronectin, proteoglycans, glycoproteins, polylactide, polyethylene glycol, polycaprolactone, polycolide, polydioxanone, polyacrylates, polyurethanes, polysulfones, peptide sequences, proteins and derivatives, oligopeptides, gelatin, elastin, fibrin, laminin, polymethacrylates, polyacetates, polyesters, polyamides, polycarbonates, polyanhydrides, polyamino acids carbohydrates, polysaccharides and modified polysaccharides, and derivatives and copolymers thereof as well as inorganic materials such as glass such as bioactive glass, ceramic, silica, alumina, calcite, hydroxyapatite, calcium phosphate, bone, and combinations of all of the foregoing.

With further regard to the hydrogels used to produce the Micro-Organospheres described herein, in some embodiments, the hydrogel is comprised of a material selected from the group consisting of agarose, alginate, collagen type I, a polyoxyethylene-polyoxypropylene block copolymer (e.g., Pluronic® F127 (BASF Corporation, Mount Olive, N.J.)), silicone, polysaccharide, polyethylene glycol, and polyurethane. In some embodiments, the hydrogel is comprised of alginate.

The gel droplets described herein may also include biologically-relevant materials. The phrase "biologically-relevant materials" may describe materials that are capable of being included in a biocompatible medium as defined herein and subsequently interacting with and/or influencing biological systems. For example, in some implementations, the biologically-relevant materials are magnetic beads (i.e., beads that are magnetic themselves or that contain a material that responds to a magnetic field, such as iron particles) that can be combined as part of the unpolymerized material to produce gel droplet that can be used in the methods and compositions (e.g., for the separation and purification of gel droplets). As another example, in other implementations, the biologically-relevant materials may include additional cells, in addition to the dissociated tissue sample (e.g., biopsy) material. In the unpolymerized mixture the dissociated tissue sample and the additional biologically relevant material in a uniform mixture or as a distributed mixture (e.g., on just one half or other portion of the gel droplet, including just in the core or just in the outer region of the formed gel droplet). In some variations the additional biologically-relevant material within the unpolymerized material may be suspended with the dissociated tissue sample in suspension, e.g., prior to polymerization of the droplet forming the gel droplet.

In some variations the biologically relevant material that may be included with the dissociated tissue sample (e.g., biopsy) material may contain a number of cell types, including preadipocytes, mesenchymal stem cells (MSCs), endothelial progenitor cells, T cells, B cells, mast cells, and adipose tissue macrophages, as well as small blood vessels or microvascular fragments found within the stromal vascular fraction.

In general, with respect to the dissociated tissue sample, e.g., biopsy, material that is included in the gel droplets described herein, these tissues may be any appropriate tissue from a patient, typically taken by biopsy. Although non-biopsy tissue may be used, in general, these tissues (and the resulting dissociated cells) may be primary cell taken from a patient biopsy as described above, e.g., by a needle biopsy. Tissues may be from a healthy tissue biopsy or from cancerous (e.g., tumor) cell biopsy. The dissociated cells may be incorporated into a gel droplet of the presently-disclosed subject matter, based on the intended use of that gel droplet. For example, relevant tissues (e.g., dissociated biopsy tissue) may typically include cells that are commonly found in that tissue or organ (or tumor, etc.). In that regard, exemplary relevant cells that can be incorporated into gel droplets of the presently-disclosed subject matter include neurons, cardiomyocytes, myocytes, chondrocytes, pancreatic acinar cells, islets of Langerhans, osteocytes, hepatocytes, Kupffer cells, fibroblasts, myoblasts, satellite cells, endothelial cells, adipocytes, preadipocytes, biliary epithelial cells, and the like. These types of tissues may be dissociated by conventional techniques known in the art. Suitable biopsied tissue can be derived from: bone marrow, skin, cartilage, tendon, bone, muscle (including cardiac muscle), blood vessels, corneal, neural, brain, gastrointestinal, renal, liver, pancreatic (including islet cells), lung, pituitary, thyroid, adrenal, lymphatic, salivary, ovarian, testicular, cervical, bladder, endometrial, prostate, vulval and esophageal tissue. Normal or diseased (e.g., cancerous) tissue may be used. In some variations, the tissue may arise from tumor tissue, including tumors originating in any of these normal tissues.

Once formed the gel droplets may be cryopreserved and/or cultured. Cultured gel droplets may be maintained in suspension, either static (e.g., in a well, vial, etc.) or in motion (e.g., rolling or agitated). The gel droplet may be cultured using known culturing techniques. Exemplary techniques can be found in, among other places; Freshney, Culture of Animal Cells, A Manual of Basic Techniques, 4th ed., Wiley Liss, John Wiley & Sons, 2000; Basic Cell Culture: A Practical Approach, Davis, ed., Oxford University Press, 2002; Animal Cell Culture: A Practical Approach, Masters, ed., 2000; and U.S. Pat. Nos. 5,516,681 and 5,559,022.

In some variations the gel droplets are formed by forming a droplet of the unpolymerized mixture (e.g., in some variations a chilled mixture) of a dissociated tissue sample and a fluid matrix material in an oil. For example, a gel droplet may be formed by combining a stream of unpolymerized material with one or more streams of the oil to form a droplet. The density of the cells present in the droplet may be determined by the dilution of the dissociated material (e.g., cells) in the unpolymerized material. The size of the gel droplet may correlate to the size of the droplet formed. In general, the gel droplet is a spherical structure having a stable geometry.

The practice of the presently disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

As used herein a drug composition may include any drug, drug dilution, drug formulation, compositions including multiple drugs (e.g., multiple active ingredients), drug formulations, drug forms, drug concentrations, combination therapies, and the like. In some variations a drug formulation refers to a formulation comprising a mixture of a drug and one or more inactive ingredients.

During culturing, the cells from the dissociated, biopsied tissue in the gel droplets can aggregate, cluster or assemble within the gel droplets. Aggregates of cells may be highly organized and may form defined morphology or may be a mass of cells that have clustered or adhered together. The organization may reflect the tissue of origin. Although in some variations the gel droplets may contain a single cell type (homotypic), more typically these gel droplets may contain more than one cell type (heterotypic).

As mentioned, the (e.g., biopsy) tissue used to form the gel droplets (e.g., the dissociated tissue) may be derived from a normal or healthy biological tissue, or from a biological tissue afflicted with a disease or illness, such as a tissue or fluid derived from a tumor. The tissue used in the gel droplets may include cells of the immune system, such as T lymphocytes, B lymphocytes, polymorphonuclear leukocytes, macrophages and dendritic cells. The cells may be stem cells, progenitor cells or somatic cells. The tissue may be mammalian cells such as human cells or cells from animals such as mice, rats, rabbits, and the like.

Generally, the cells are first dissociated or separated from each other before forming the gel droplets. Dissociation of cells may be accomplished by any conventional means known in the art. Preferably, the cells are treated mechanically and/or chemically, such as by treatment with enzymes. By 'mechanically' we include the meaning of disrupting connections between associated cells, for example, using a scalpel or scissors or by using a machine such as an homogenizer. By 'enzymatically' we include the meaning of treating the cells with one or more enzymes disrupt connections between associated cells, including for example any of collagenase, dispases, DNAse and/or hyaluronidase. One or more enzymes may be used under different reaction conditions, such as incubation at 37° C. in a water bath or at room temperature.

The dissociated tissue may be treated to remove dead and/or dying cells and/or cell debris. The removal of such dead and/or dying cells may be accomplished by any conventional means known to those skilled in the art, for example using beads and/or antibody methods. It is known, for example, that phosphatidylserine is redistributed from the inner to outer plasma membrane leaflet in apoptotic or dead cells. The use of Annexin V-Biotin binding followed by binding of the biotin to streptavidin magnetic beads enables the separation of apoptotic cells from living cells. Similarly, removal of cell debris may be achieved by any suitable technique in the art, including, for example, filtration.

The dissociated cells may be suspended in a carrier material prior to combining with the fluid matrix material, and/or the fluid matrix material may be referred to as a carrier material. In some variations the carrier material may be a material that has a viscosity level that delays sedimentation of cells in a cell suspension prior to polymerization and formation of the gel droplets. A carrier material may have sufficient viscosity to allow the dissociated biopsy tissue cells to remain suspended in the suspension until polymerization. The viscosity required to achieve this can be optimized by the skilled person by monitoring the sedimentation rate at various viscosities and selecting a viscosity that gives an appropriate sedimentation rate for the expected time delay between loading the cell suspension into the apparatus forming the gel droplets forming the gel droplets by polymerizing the droplets of the unpolymerized material including the cells. In some variations the unpolymerized material may be flowed or agitated by the apparatus even where lower viscosity materials are used, in order to keep the cells in suspension and/or distributed as desired.

As mentioned above, in some variations the unpolymerized mixture, including the dissociated tissue sample and the fluid matrix material may include one or more components, e.g., biologically-relevant materials. For example, a biologically-relevant material that may be included may include any of: an extracellular matrix protein (e.g. fibronectin), a drug (e.g. small molecules), a peptide, or an antibody (e.g., to modulate any of cell survival, proliferation or differentiation); and/or an inhibitor of a particular cellular function. Such biologically-relevant materials may be used, for example, to increase cell viability by reducing cell death and/or activation of cell growth/replication or to otherwise mimic the in vivo environment. The biologically-relevant materials may include or may mimic one or more of the following components: serum, interleukins, chemokines, growth factors, glucose, physiological salts, amino acids and hormones. For example, the biologically-relevant materials may supplement one or more agents in the fluid matrix material. In some variations, the fluid matrix material is a synthetic gel (hydrogel) and may be supplemented by one or more biologically-relevant materials. In some variations the fluid matrix is a natural gel. Thus, the gel may be comprised of one or more extracellular matrix components such as any of collagen, fibrinogen, laminin, fibronectin, vitronectin, hyaluronic acid, fibrin, alginate, agarose and chitosan. For example, MATRIGEL comprises bioactive polymers that are important for cell viability, proliferation, development and migration. For example, the matrix material may be a gel that comprises collagen type 1 such as collagen type 1 obtained from rat tails. The gel may be a pure collagen type 1 gel or may be one that contains collagen type 1 in addition to other components, such as other extracellular matrix proteins. A synthetic gel may refer to a gel that does not naturally occur in nature. Examples of synthetic gels include gels derived from any of polyethylene glycol (PEG), polyhydroxyethyl methacrylate (PHEMA), polyvinyl alcohol (PVA), poly ethylene oxide (PEO).

Forming Gel Droplets

Figures 2, 3:
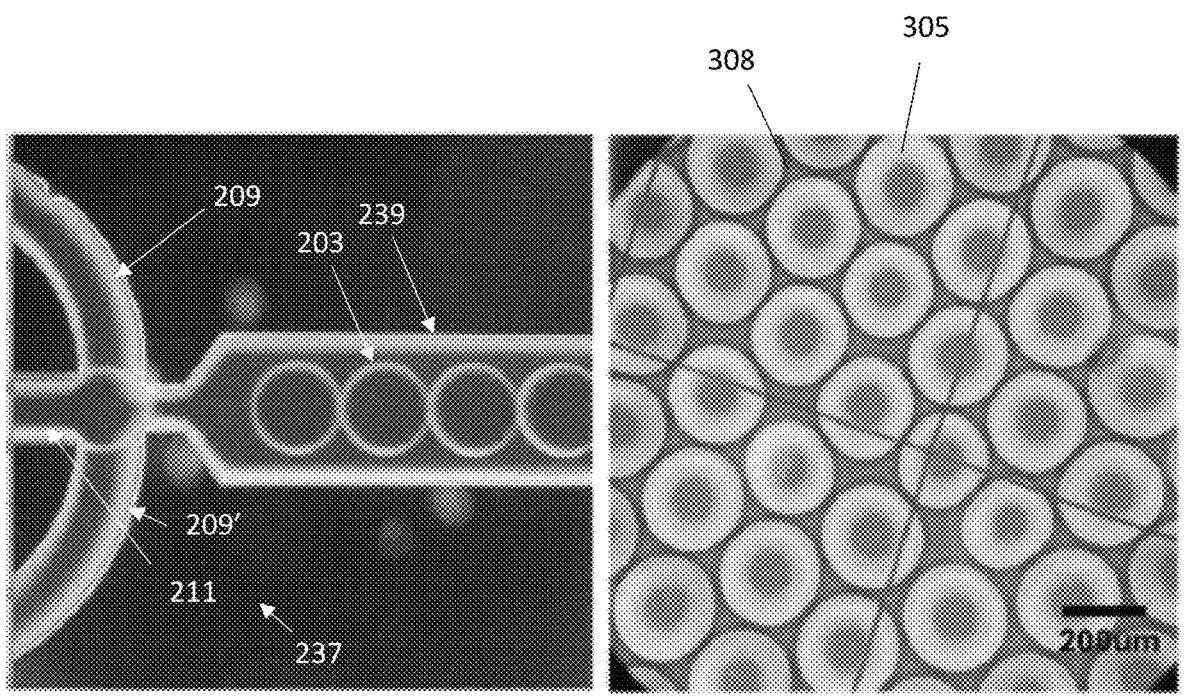
FIG. 2 is an image of a portion of a prototype microfluidics assembly for an apparatus for forming gel droplets, and in particularly micro-organospheres, illustrating the formation of micro-organospheres.
FIG. 3 illustrates a plurality of gel droplets as described herein, shortly after polymerization, suspended in the oil.

FIG. 1 illustrates one example of plurality of gel droplets that have been formed by combining dissociated tissue cells with a matrix material within an oil carrier to allow the matrix material to polymerize into spherical gel droplets 103, as shown. For example, FIG. 1 illustrates one example of a channel region 139 that is transparent and contains a plurality of gel droplets 103 each containing a predetermined number of cells 105. The cells may be formed within a microfluidics device, such as that shown in FIG. 2, for example. In FIG. 2, the microfluidics device includes a junction region 237, so that a channel carrying the unpolymerized mixture 211 intersects one or more (e.g., two) channels 209 carrying oil that is immiscible with the unpolymerized mixture. As the unpolymerized mixture is pressurized to flow at first rate out of the first channel 211, the flowing oil in the intersecting channels, 209, 209', permit a predefined amount of the unpolymerized mixture to pass before pinching it off to form a droplet 203 that is passed into the outlet channel 239. Thus, in some variations, a minced (e.g., dissociated) clinical (e.g., biopsy or resected) sample of tissue, such as <1 mm in diameter, may be is mixed with a temperature-sensitive gel (i.e. MATRIGEL, at 4 degrees C.) to form the unpolymerized mixture. This unpolymerized mixture may be placed into the microfluidic device that may generates droplets (e.g., water-in-oil droplets) that are uniform in volume and material composition. Simultaneously, the dissociated tumor cells may be partitioned into these droplets. The gel in the unpolymerized material may solidify upon heating (e.g., at 37 degrees C.), and the resulting gel droplets may be formed. These gel droplets (shown here as micro-organospheres) are compatible with traditional 3D cell culture techniques. FIG. 3 illustrates a plurality of gel droplets 305 formed as described above, suspended in the oil 308.

In the exemplary microfluidics chip illustrated above, the junction is shown as a T- or X-junction in which the flow focusing of the microfluidics forms the controllable size of the gel droplets. In some variations, rather than a microfluidics chip, the droplets may be formed by robotic micropipetting, e.g., into an immiscible fluid and/or onto a solid or gel substrate. Alternatively in some variations the droplets of unpolymerized material may be formed in the requisite dimensions and reproducibility by micro-capillary generation. Other example of techniques that may alternatively be used for forming the gel droplets in the specified size range and reproducibility from the unpolymerized material may include colloid manipulation, e.g., via external forces such as acoustics, magnetics, inertial, electrowetting, or gravitational.

Figure 4A:
FIG. 4A shows on example of a plurality of gel droplets within oil shortly after formation of the gel droplets.

FIG. 4A shows an example of gel droplets in oil formed as described above. The gel droplets may be used for an assay immediately, cultured and/or stored (e.g., by cryopreservation). However, it has been found that the viability, particularly in culture, is negatively affected by including oil with the gel droplets. Further, the presence of oil may make it difficult or impossible to accurately assay and/or manipulate the gel droplets. For example, the gel droplets within (or including some) oil may clump or cluster together, preventing isolation and manipulation of individual gel droplets. Thus, it is desirable to remove the oil.

Figure 4B:
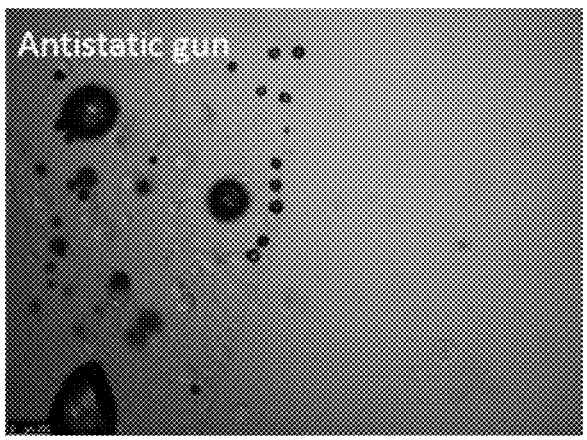
FIG. 4B shows gel droplets from which oil has been removed using an antistatic gun, for comparison to other oil-removing (e.g., demulsifying) techniques, showing some gel droplets but additional oil and associated debris. Asterisks indicate gel droplets comprising dissociated cells.
Figure 4C:
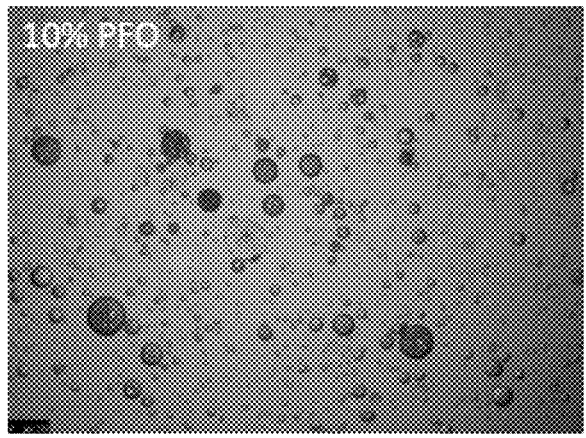
FIG. 4C shows gel droplets following the removal of oil using 10% PFO, as previously described. Asterisks indicate gel droplets comprising dissociated cells.
Figure 4D:
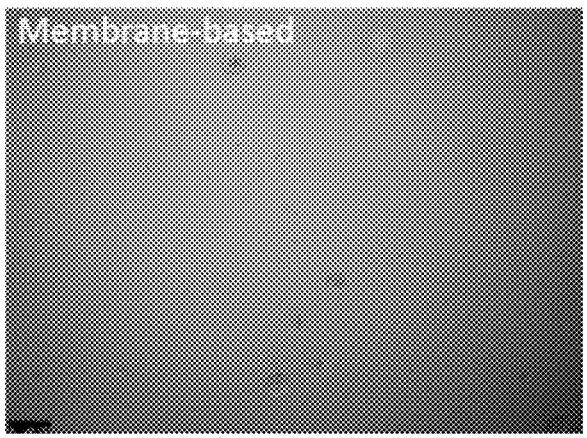
FIG. 4D shows gel droplets following removal of the oil using a porous hydrophobic surface (e.g., membrane) as described herein. Asterisks indicate gel droplets comprising dissociated cells.

FIGS. 4B and 4C illustrate examples of method that may be used for removing oil from the gel droplets; these techniques are less thorough and effective, and may in fact be more complicated, than the methods described herein using a porous hydrophobic surface. For example, FIG. 4B illustrates the gel droplets for which an antistatic gun was used to remove oil. In this example, as can be seen in FIG. 4B, the oil was not completely removed, and further, the resulting gel droplets (shown here by asterisks) are left with oil and debris, possibly resulting from destruction of some gel droplets during the demulsification step. Alternatively, FIG. 4C illustrates the use of a chemical demulsification agent, in this case PFO (10% PFO) used to remove oil from the gel droplets. In this case, the demulsification agent (e.g., PFO) may remove the oil, however, the demulsification agent may also have associated toxicity with respect to the gel droplets. Further, the associated washing/rinsing steps may add additional time and cost to the purification and processing steps. In FIG. 4C, the gel droplets are recovered from the oil phase and resuspended, e.g., into PBS via PFO (perfluoro octanol) and centrifugation. This may separate the immiscible fluid from the gel droplets. Thus, these gel droplets, including tumor-based organospheres, can be successfully grown FIG. 4D illustrates gel droplets that have been processed to remove the oil using a porous hydrophobic surface (e.g., membrane) as described herein. As can be shown in FIG. 4D, the resulting gel droplets (also indicated by asterisks) generally appear 'cleaner,' with less debris and with little or no residual oil.

Figure 5:
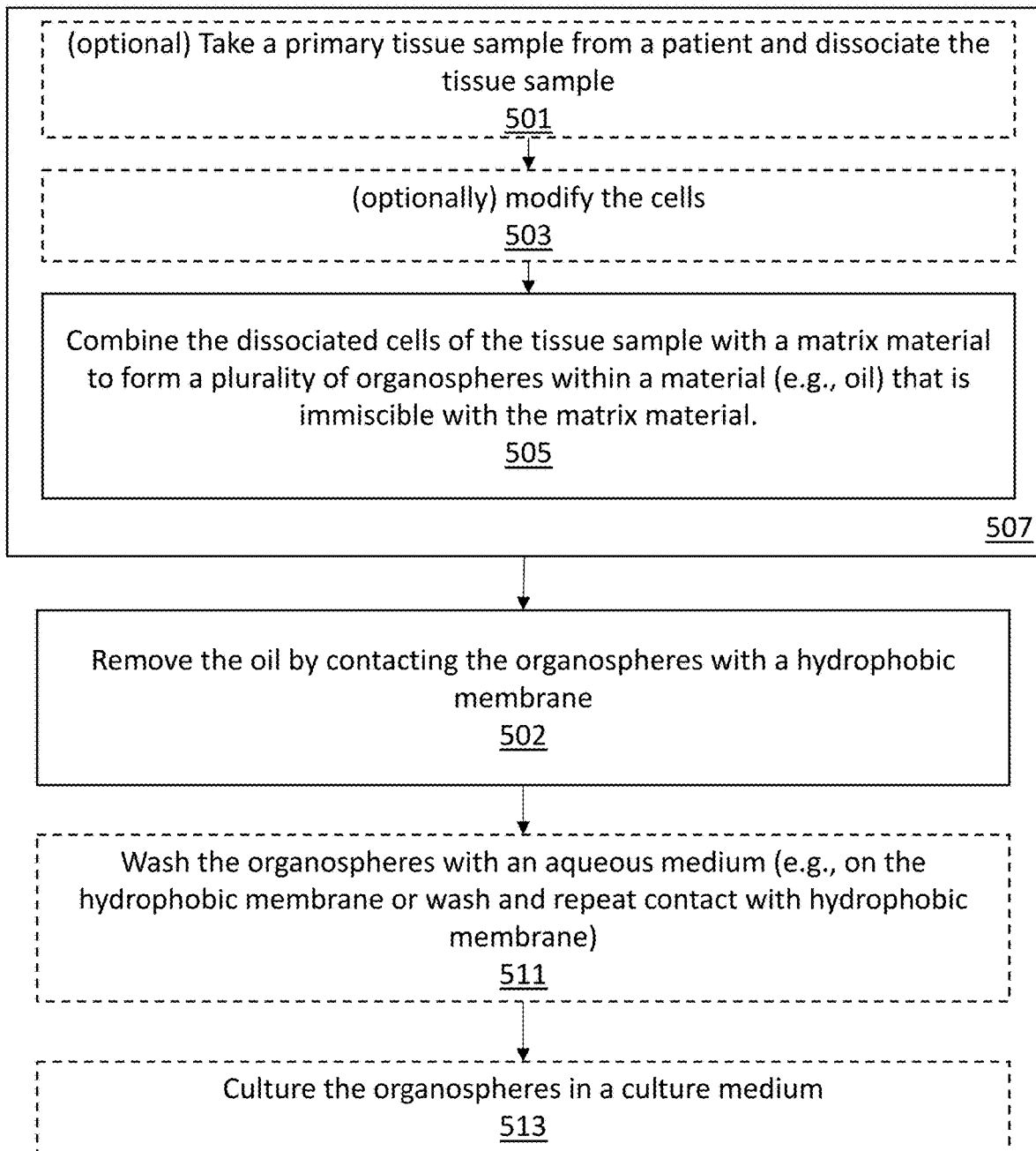
FIG. 5 schematically illustrates one example of a method for processing gel droplets including removing oil from the gel droplets using a porous hydrophobic surface, as described herein.

FIG. 5 illustrates one example of a general method of forming/and or processing (including removing oil) gel droplets using a porous hydrophobic surface. In FIG. 5, the method may optionally begin with a primary tissue sample (or other source of cells to be included in the gel droplets); the tissue sample may be dissociated and/or suspended 501. As mentioned above, in some variations the cells may be modified 503. The dissociated cells may then be combined with an unpolymerized matrix material 505, and streamed into an oil to form the gel droplets within the oil; the matrix material with the combined dissociated cells (and any additional components) may then be polymerized, as described above, e.g., by increasing the temperature. These steps may generally be part of a step or multiple steps for forming the gel droplets 507, and all or some of these steps may be automated, e.g., by an apparatus.

As shown in FIG. 5, the oil may then be removed using a porous hydrophobic surface (e.g., membrane) 502. In some cases it may be preferable to remove excess oil from the gel droplets first, before exposing to the porous hydrophobic surface, as a rough method to remove the bulk of the oil. For example, the gel droplets may be separated from some of the oil by spinning, followed by removing of the oil layer (e.g., the bottom layer) by pipetting. Alternatively, the oil and gel droplets suspended therein may be directly placed into contact with the porous hydrophobic surface. In any event, the gel droplets may be de-emulsified using a porous hydrophobic membrane, as described in greater detail below. This step may remove all or substantially all of the oil (e.g., greater than 99%), and may be quick and easy to perform.

Once the oil has been removed, the gel droplets may be separated from the porous hydrophobic surface (e.g., membrane), e.g., by washing and/or eluting using a buffer and/or cell culture media 511 into a container. In some cases the gel droplets may be used immediately; alternatively all or some of the gel droplets may be cultured 513, and/or cryopreserved.

Figure 6:
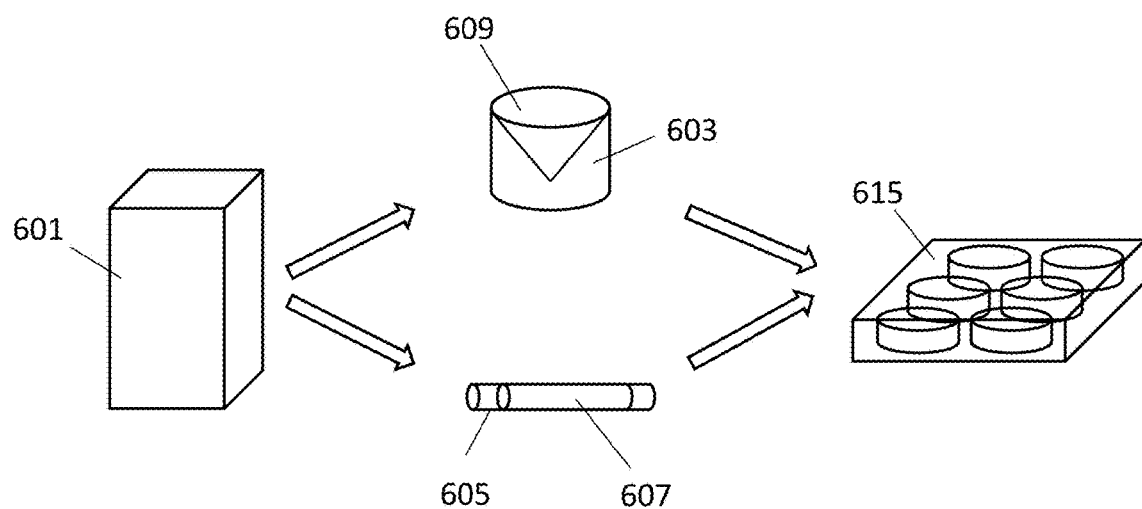
FIG. 6 diagrammatically illustrates one example of an apparatus configured to form gel droplets, including removal of oil from the gel droplets, as described herein.

Also described herein are apparatuses that may perform any of these methods. For example, FIG. 6 illustrates one example of an apparatus that may include components to automate all or some of these steps. For example, in FIG. 6, the apparatus may include a microfluidics component 601, which may include a plurality of channels (e.g., as part of a microfluidics chip) and may further include one or more ports for receiving the unpolymerized matrix, the dissociated cells, and/or the oil, so that they may be combined as shown and described in reference to FIG. 2, above. Thus, the apparatus may include a fluidic (e.g., microfluidic) processor comprising a plurality of channels, including a first channel configured to receive a dissociated tissue sample comprising dissociated cells and an unpolymerized matrix material, and a second channel configured to receive an oil and to intersect with the first channel to form polymerized gel droplets suspended in the oil. The processor may also include a controller having one or more microprocessors, that may control the operation of the apparatus and regulate the formation and processing of the gel droplets. In addition, the apparatus may include a de-emulsifying portion 603, 605 that may include a porous hydrophobic surface (e.g., membrane) 609, 607 in fluid communication with the fluidic processor and configured to remove oil from the gel droplets. Finally, the apparatus may include an elution channel that is configured to elute the gel droplets into one or more containers, such as a multi-well plate 615.

In general, the de-emulsifying portion may include any appropriate porous hydrophobic surface, such as a hydrophobic membrane, and particularly a membrane having pores of between 0.1 μm to 500 μm (e.g., between 0.1 μm and 400 μm, between 0.1 μm and 300 μm, between 0.1 μm and 250 μm, between 0.1 μm and 200 μm, between 0.01 μm and 150 μm, between 0.01 μm and 100 μm, etc.). In FIG. 6, the de-emulsifying portion shows, on the top, a porous hydrophobic membrane 609 formed into a funnel that may be used to apply a solution (e.g., an oil-containing solution) of gel droplets onto/into in order to remove the oil by absorption into or through the membrane. FIG. 6 also shown an alternatively embodiment of the de-emulsifying portion that includes a channel 605, within which a region of porous hydrophobic membrane 607 is arranged. The solution of gel droplets, including oil, may be applied at the first end of the channel, and the solution, including the gel droplets, may be run thought the channel (e.g. column, etc.) which may be slightly (between 1 degree and 30 degrees) at an angle relative to the horizontal, so that the fluid may be driven down the channel/column during removal of the oil. In some variations the angle of the hydrophobic surface (formed into a tunnel 605 in the bottom of FIG. 6), may be changed.

Figure 7:
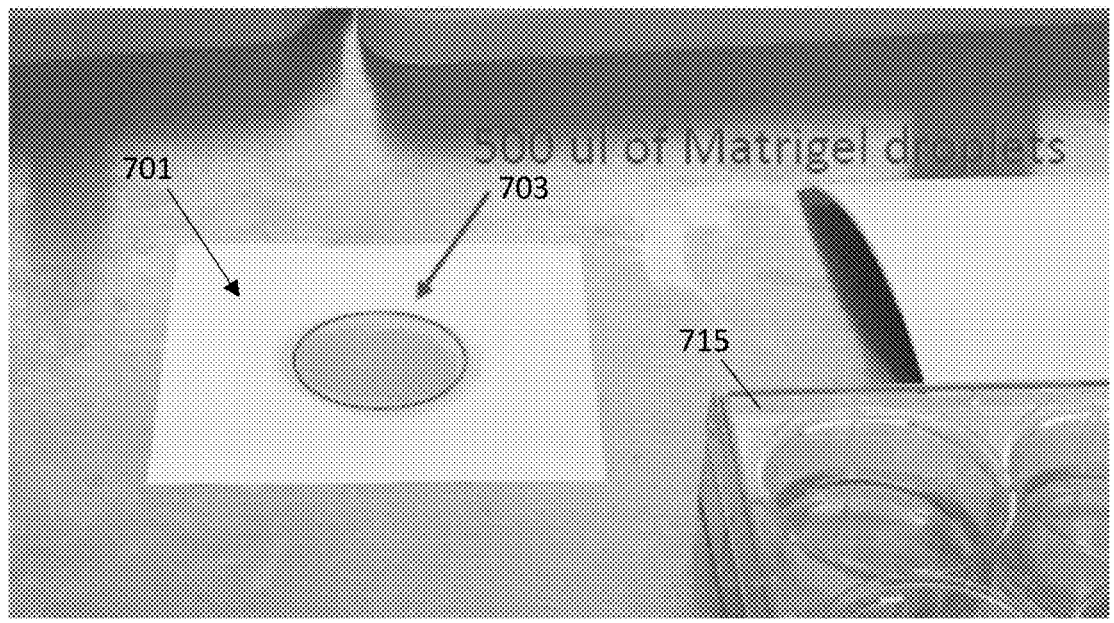
FIG. 7 illustrates one method of manually using a hydrophobic surface to remove oil from gel droplets as described herein.

For example, FIG. 7 illustrates one example of the removal of oil from a plurality of gel droplets. In FIG. 7 a sheet of hydrophobic membrane, such as a PVDF transfer membrane having a pore size of 0.45 µm, is placed on a surface (e.g., of a table) and 500 µL of an oil in which a plurality of gel droplets ("Matrigel droplets") have been formed. The gel droplets in oil are applied to the surface of the membrane allowing the oil to absorb into and through the membrane, while the gel droplets remain on top. In practice, the gel droplets may then be optionally be washed by applying buffer or media directly onto the gel droplets on the membrane one or more times (e.g., 3×). In some variations the gel droplets may be moved, via the washing, to another portion of the membrane, to allow further removal of the oil by the hydrophobic membrane. The gel droplets may then be rinsed into a container, shown in this example as a multi-well plate 715. Analysis of this method has shown that virtually all (e.g., greater than 99%) of the oil is removed in this manner. Further this type of handling does not negatively affect the gel droplets.

Indeed, an analysis of fresh gel droplets shortly after processing with a hydrophobic membrane to remove oil from the gel droplets without the use of a chemical demulsifying agent shows that the overall viability of the cells within the processed gel droplets is greater than that of gel droplets processed by other techniques (such as shown in FIG. 4B-4C) to remove oil. In general, the more residual oil left on the gel droplets, the less growth of the cells in the gel droplets was found. Further, the methods described herein were generally significantly faster, requiring less washing and repeating of washing/rinsing steps. Further the resulting gel droplets tended to look clearer, with less gel droplet/cell debris.

For example, FIGS. 8A-8D illustrate one example of gel droplets formed by the method of processing described herein, and allow comparison between low (4×, FIGS. 8A, 8B) and higher (10×, FIGS. 8C and 8D). In FIGS. 8A and 8C, each gel droplets includes one cell and the gel droplets have been cleaned to remove all of the oil, as shown. Similarly, FIGS. 8B and 8D show gel droplets having 20 cells each.

Figure 9A:
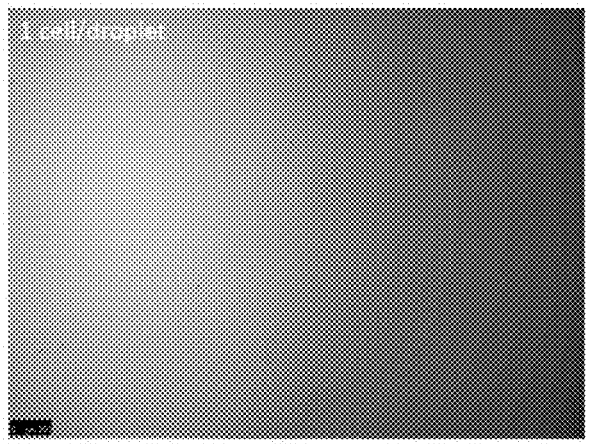
FIGS. 9A and 9B show examples of gel droplets having 1 cell/droplet (FIG. 9A) or 20 cells/droplet (FIG. 9B) similar to those shown in FIGS. 8A-8B, two days after removal of oil using a hydrophobic membrane as described herein.
Figure 9B:
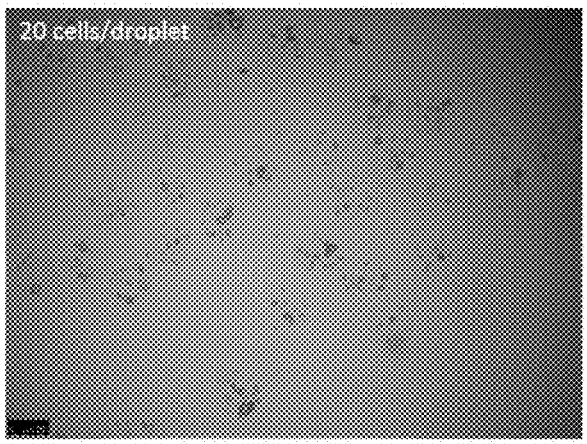
Figure 10A:
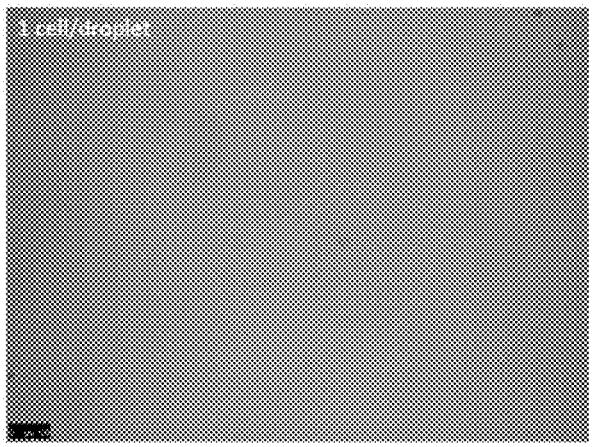
FIGS. 10A and 10B show examples of gel droplets having 1 cell/droplet (FIG. 10A) or 20 cells/droplet (FIG. 10B) similar to those shown in FIGS. 8C-8D, two days after removal of oil using a hydrophobic membrane as described herein.
Figure 10B:
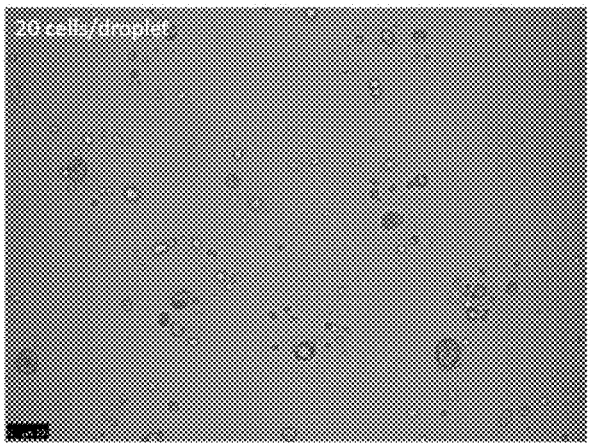

As mentioned above, the gel droplets formed as described herein have been seen to have significantly increased viability over time in culture as compared to de-emulsifying techniques or not de-emulsifying. These methods may also be particularly effective over time in culture, as shown in FIGS. 9A-11B. For example, FIGS. 9A-9B illustrate an example of a method including the use of a hydrophobic membrane (porous hydrophobic membrane) as described herein to remove oil from the gel droplets. In FIGS. 9A-9C, gel droplets having 1 (FIG. 9A) or 20 (FIG. 9B) cells (on average) are shown at low magnification (e.g., 4×), two days after forming. As can be seen, the resulting gel droplets are very 'clean' including the surrounding medium. FIG. 10A-10B show a slightly enlarged view of similar gel droplets after 2 days in culture.

Figure 11A:
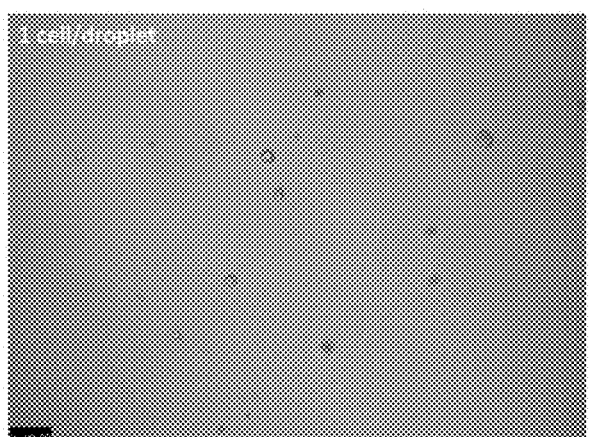
FIGS. 11A and 11B show examples of gel droplets having 1 cell/droplet (FIG. 11A) or 20 cells/droplet (FIG. 11B) similar to those shown in FIGS. 8C-8D, three days after removal of oil using a hydrophobic membrane as described herein.
Figure 11B:
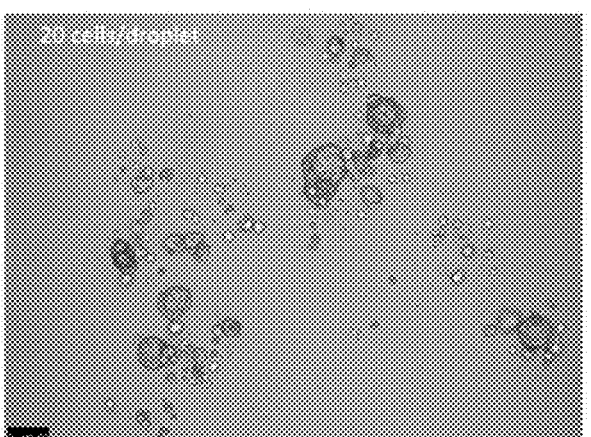

Finally, FIGS. 11A-11B illustrate similar gel droplets after three days in culture, showing widespread and robust growth within the gel droplets. The gel droplets shown in FIG. 11A-11B are also shown at 10× magnification. As mentioned, the gel droplets have been washed on the hydrophobic membrane in order to remove the oil. This oil may be removed relatively quickly after forming the Micro-Gel droplets in order to prevent harm to the cells within the Micro-Organosphere.

Figure 12A:
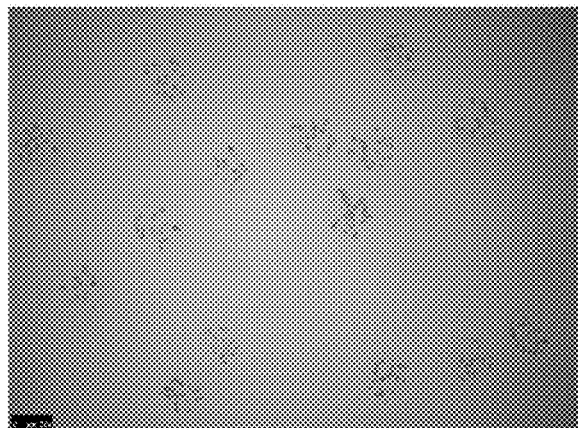
FIGS. 12A-12B show examples of gel droplets formed from VERO cells having 20 cells/droplet at 4× (FIG. 14A) or 10× (FIG. 14B) magnification, respectively.
Figure 12B:
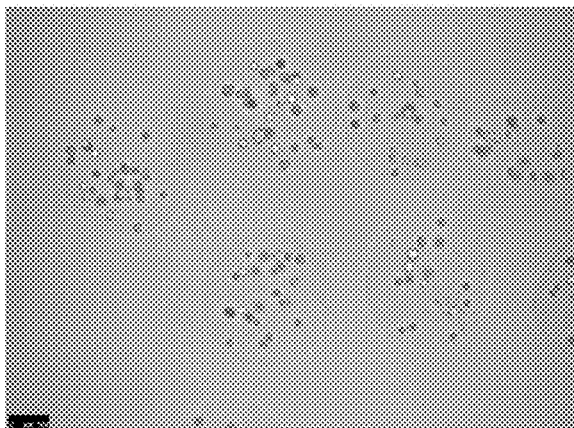
Figure 13A:
FIGS. 13A-13B show examples of gel droplets formed from 293T cells having 20 cells/droplet at 4× (FIG. 13A) or 10× (FIG. 13B) magnification, respectively.
Figure 13B:
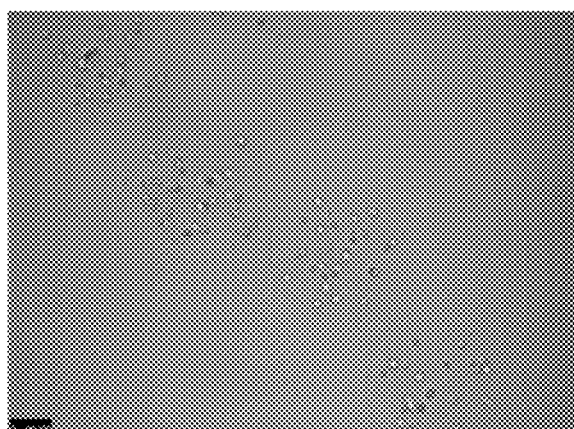
Figure 14A:
FIGS. 14A-14B show examples of gel droplets formed from 293 ACE2 cells having 20 cells/droplet at 4× (FIG. 14A) or 10× (FIG. 14B) magnification, respectively.
Figure 14B:
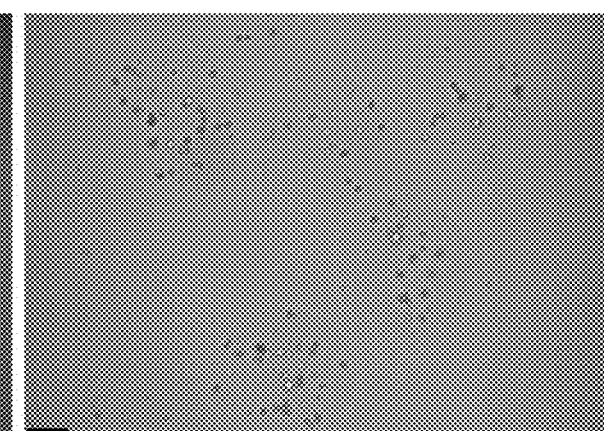
Figure 15A:
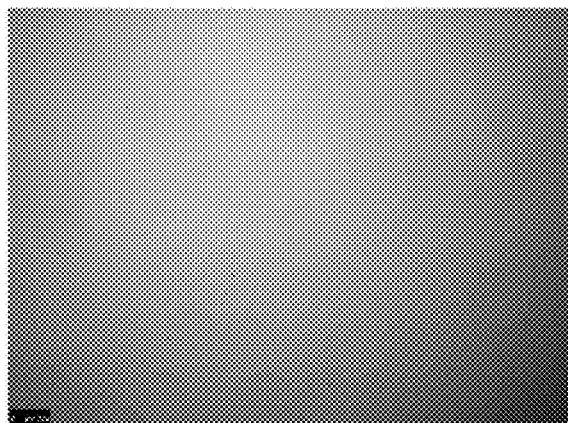
FIGS. 15A-15B show examples of gel droplets formed from CRC19-106 cells having 1 cell/droplet (FIG. 15A) at 4× or 10× (FIG. 15B) magnification, respectively.
Figure 15B:
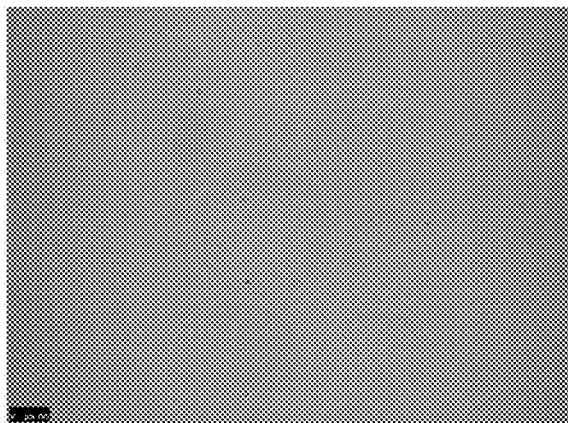
Figure 16A:
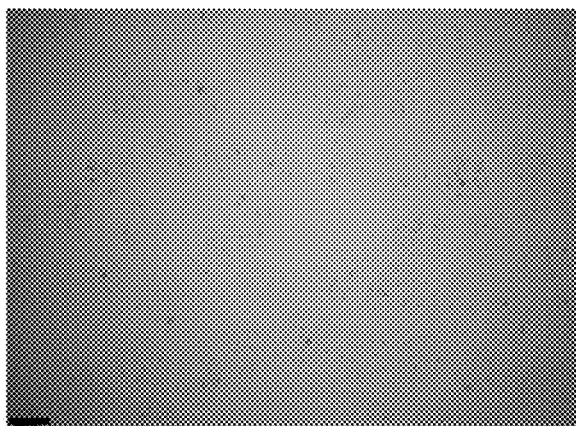
FIGS. 16A-16B show examples of gel droplets formed from CRC-1916 cells having 20 cells/droplet at 4× (FIG. 16A) or 10× (FIG. 16B) magnification, respectively.
Figure 16B:
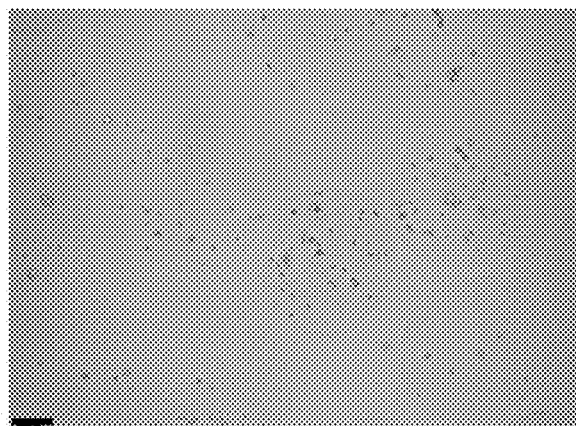
Figure 17A:
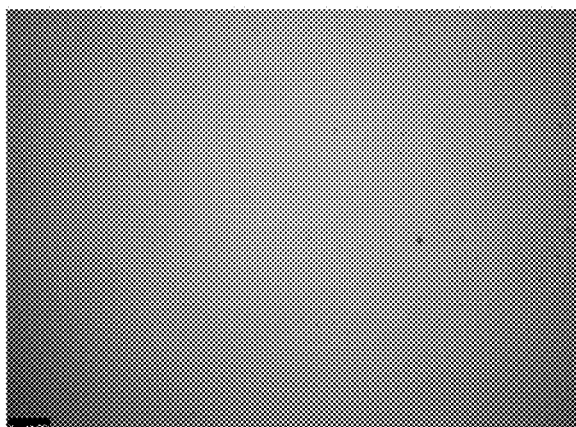
FIGS. 17A-17B show examples of gel droplets formed from CRC19817 cells having 1 cell/droplet (FIG. 17A) or 10× (FIG. 17B) magnification, respectively.
Figure 17B:
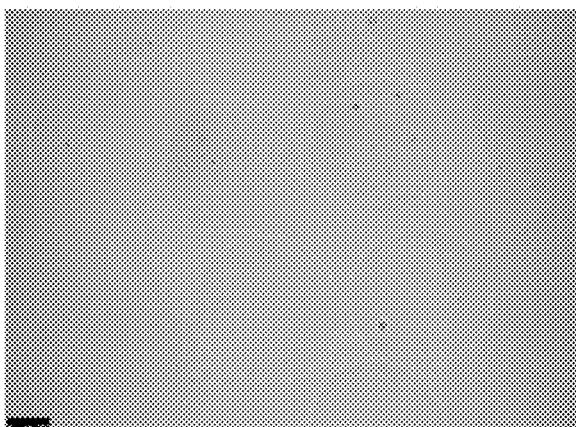

The methods and apparatuses described herein may generally work with virtually any cell type for which a gel droplet may formed. For example, FIGS. 12A-12B, 13A-13B, 14A-14B, 15A-15B, 16A-16B, 17A-17B, 18A-18B, 19A-19B, 20A-20B and 21A-21B all show different cell or tissue types used to from gel droplets, for which the methods described herein to remove oil from the gel droplets may be followed. For example, FIGS. 12A-12B illustrate VERO cells (20 cells/gel droplet), FIGS. 13A-13B illustrate 293T cells, and FIGS. 14A-14B illustrate gel droplets including 293 ACE2 cells, showing both low magnitude (4×, left) and high magnitude (10×, right). FIGS. 15A-15B illustrate gel droplets including CRC19-106 cells at 1 cell/gel droplet, FIGS. 16A-16B also show CRC19-106 cells, but at 20 cells/gel droplet, FIGS. 17A-17B show CRC19817 cells having 1 cell/gel droplet, and FIGS. 18A-18B illustrate gel droplets including CRC19178 cell having 20 cells/gel droplet, all having oil removed using hydrophobic membrane, as described herein. FIGS. 19A-19B shown CRC19245 cells at 1 cell/gel droplet, and FIGS. 20A-20B show CRC19245 cells at 20 cells/gel droplet. Finally, FIGS. 21A-21B show low and high magnification, respectively, of mouse intestine organoids including 20 cells/gel droplet.

In any of the examples described herein, the method may be a method of forming organospheres (e.g., microorganospheres) from cells that have been cultured or isolated (e.g., by dissociation) from tissue. The sample may be received for processing and may be processed in a very gentle way, including using an automated or semi-automated system. For example, the sample may be received and processed in a chilled, temperature-regulated manner, for example, by cooling the temperature of the sample (including any media in which the cells are held) and the liquid basement membrane material to a cell processing temperature or temperature range (e.g. cooled to less than 25, less than 20 degrees C., less than 19 degrees C., less than 18 degrees C., less than 17 degrees C., less than 16 degrees C., less than 15 degrees C., less than 14 degrees C., less than 13 degrees C., less than 12 degrees C., less than 11 degrees C., less than 10 degrees C., less than 9 degrees C., less than 8 degrees C., less than 7 degrees C., between about 5-25 degrees C., between about 5-20 degrees C., etc.). Thus, the cells may be suspended in an aqueous solution maintained at the cell processing temperature (or temperature range). The liquid basement membrane material may also be maintained within the same cell processing temperature range. The cells may then be combined with a liquid basement membrane matrix (such as, but not limited to MATRIGEL). The liquid basement membrane material may be diluted to a predetermined concentration by the combination.

The cells in the liquid basement membrane material may then be formed into droplets by extruding them into an oil. The droplets may be formed by flowing a predetermined amount (and/or at a predetermined flow rate) of the combined cells and liquid basement membrane material into the oil. The oil may be a pool or a stream. Droplets may be formed from the cells in the liquid basement membrane matrix so that each droplet includes a predetermined amount of cells (e.g., between 1-500 cells, between 1-400 cells, between 1-300 cells, between 1-200 cells, between 1-100 cells, etc.). The droplets formed in the oil may then be polymerized by increasing the temperature. For example the temperature may be increased to a polymerization (e.g., to 30 degrees C. or greater, 32 degrees C. or greater, 35 degrees C. or greater, between 30-38 degrees C., between 32-37 degrees, etc.) to polymerize the gel droplet. The temperature may be increased by increasing the temperature of the oil. In some examples, it may be beneficial to combine the droplet of cells and liquid basement membrane material in an oil that is at the same initial temperature and increase the temperature of the surrounding oil after formation of the droplet. In some examples, the droplets of basement membrane material including the cells may be added into an oil that is at a temperature that is higher than the cell processing temperature (or cell processing temperature range). For example, the oil may be maintained at the polymerization temperature. Warming the droplets of the combined cells and the liquid basement membrane matrix may polymerize the liquid basement membrane matrix material within the oil. Thereafter, the oil may be removed as described herein, and the cells may be cultured to form the organospheres (e.g., microorganospheres). For example, the droplets may be placed into contact with a hydrophobic membrane so that the oil is removed from the gel droplets through or into the hydrophobic membrane either before adding an aqueous (e.g., culture) media, after rinsing in aqueous culture media, or while adding the aqueous culture media, as described above.

This process has proved to be extremely effective at increasing the viability of cells within the resulting organospheres (e.g., microorganospheres). For example, as compared with other method of removing the oil, the viability of even the most sensitive cell types increased by greater than 20-50%.

For example, FIGS. 22A-22C illustrate an example of organospheres (e.g., microorganospheres) formed as described above from induced pluripotent stem cells. Induced pluripotent stem cells (iPSCs) may be extremely fragile. In FIG. 22A, microorganospheres were formed from iPSCs as described above, in oil, and the oil was removed by contacting the microorganospheres with a hydrophobic membrane, in this example, a sheet of hydrophobic Polyvinylidene difluoride (PVDF), formed into a surface (e.g., channel, funnel, etc.) through which the microorganospheres may be flowed, either before or after (or during) the addition of an aqueous (e.g., media) solution. By day 3 (shown in FIG. 22B) the majority of the resulting microorganospheres were viable and the iPSCs within the microorganospheres had increased in size and number. FIG. 22C shows the same microorganospheres at day 7. These microorganospheres were able to form "minibrain" structures.

Figure 23A:
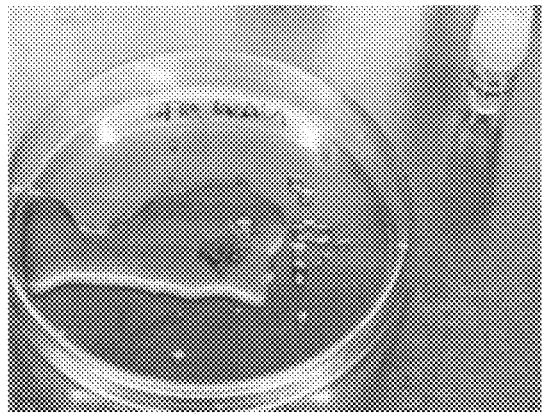
FIGS. 23A-23F illustrate micro-organospheres ("gel droplets") successfully formed as described herein from a variety of cadaver (autopsy) tissues.
Figure 23B:
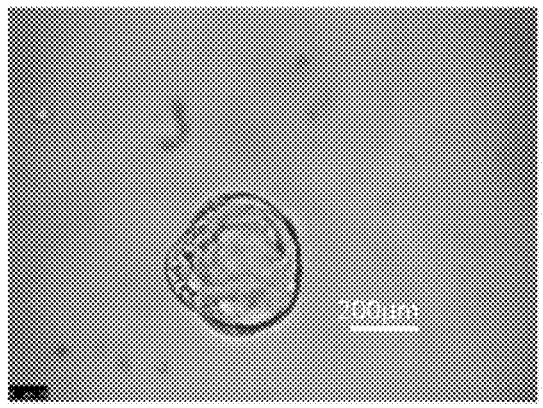
Figure 23C:
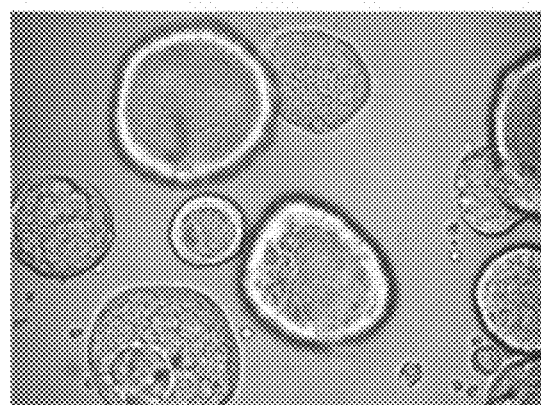
Figure 23D:
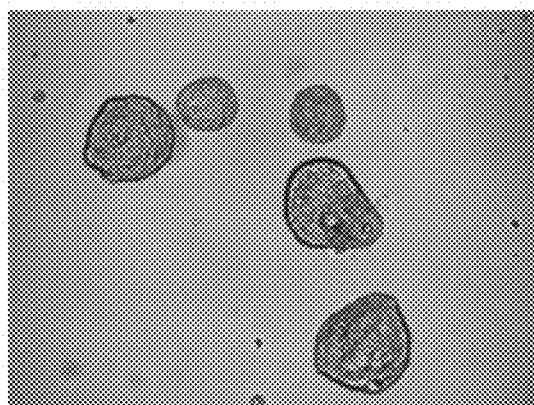
Figure 23E:
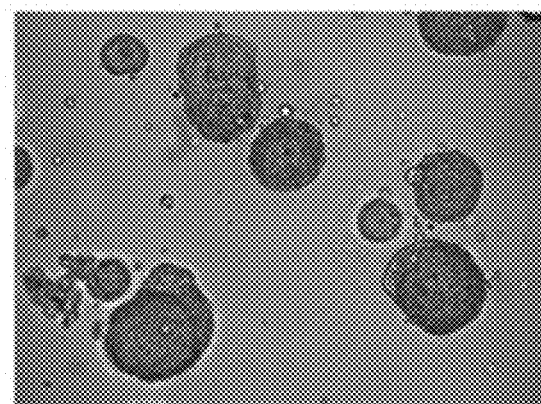
Figure 23F:
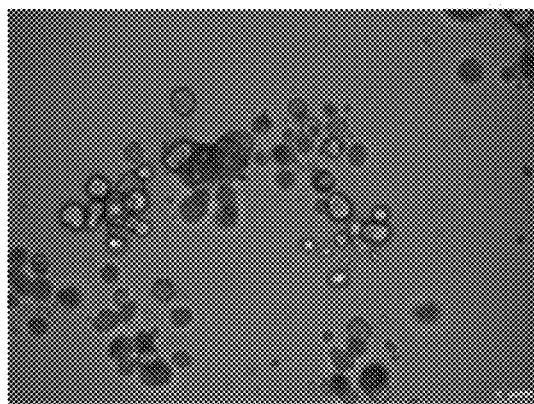
Figure 23H:
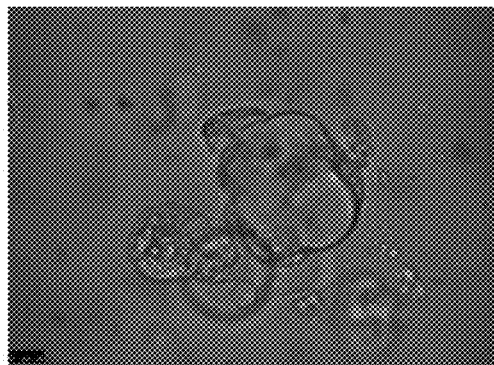
FIG. 23H shows examples of micro-organospheres formed using esophagus tissue.
Figure 23I:
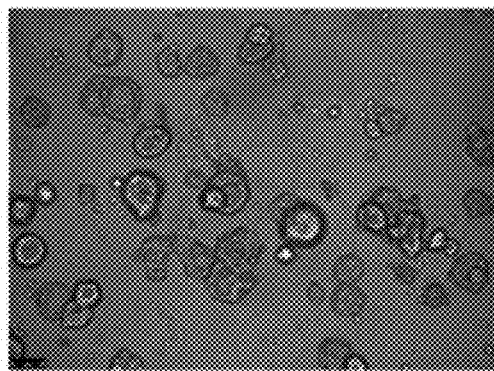
FIG. 23I shows examples of micro-organospheres formed using intestinal tissue.
Figure 23J:
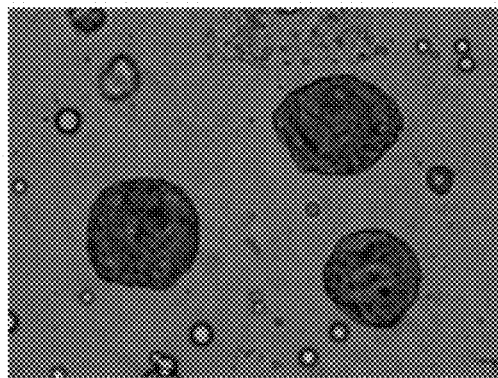
FIGS. 23J and 23K show examples of micro-organospheres formed using liver tissue. The micro-organospheres shown in FIGS. 23B-
Figure 23K:
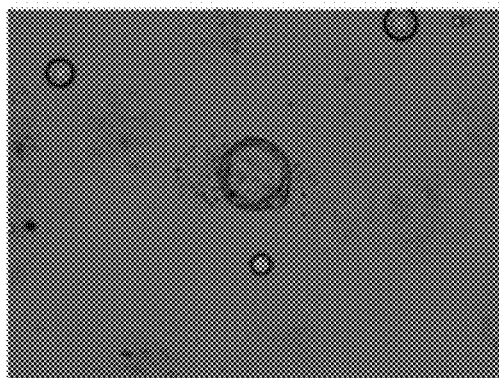

The methods described herein were generally successful for a variety of different cells including cultured and isolated (e.g., dissociated) cells. For example, FIGS. 23A-23J illustrate the results of the methods described herein on a variety of different cell types isolated from human autopsy tissue. FIG. 23A shows an example of a sample of tissue (olfactory tissue) removed as part of an autopsy. This tissue was processed as described herein, to dissociate olfactory cells and to form microorganospheres from one or more olfactory cell types. For example, FIG. 23B shows one example of a microorganospheres formed from the olfactory cells isolated as described herein. Other cell types similarly isolated and processed to form microorganospheres as described herein include distal lung cells (FIG. 23C), tracheal cells (FIG. 23D), proximal lung cells (FIG. 23E), sinonasal cells (FIG. 23F), esophageal cells (FIG. 23G), intestinal cells (FIG. 23H) and liver cells (FIGS. 23I-23J).

Although the methods and apparatuses described herein are described in the context of gel droplets that include (and support) biological tissue, such as dissociated cells, including tumor cells, it should be understood that these methods and apparatuses may be used for any gel droplets, with or without biological tissue within the droplet. In particular, these methods an apparatuses may be useful for removing oil from on or around gel droplets, with or without biological tissue within the droplet, including but not limited to gel droplets that are small (e.g., having a diameter of about 2 mm or less (e.g., 1.5 mm or less, 1.0 mm or less, 0.9 mm or less, 0.8 mm or less, 0.7 mm or less, 0.6 mm or less, 0.5 mm or less, etc., between 50-500 µm, about 50-600 µm, about 50-750 µm, about 50-900 µm, about 50 µm to 1 mm, etc.).

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An apparatus for forming gel droplets, the apparatus comprising:
    a fluidic processor comprising a plurality of channels, including:
    a first channel configured to receive a dissociated tissue sample comprising dissociated cells and an unpolymerized matrix material, and
    a second channel configured to receive an oil and to intersect with the first channel to form polymerized gel droplets suspended in the oil;
    a demulsifying portion comprising a hydrophobic membrane in fluid communication with the fluidic processor and configured to remove the oil from the polymerized gel droplets; and
    an elution channel configured to elute the polymerized gel droplets from the demulsifying portion.

2. The apparatus of claim 1, wherein the demulsifying portion comprises a chamber at least partially formed by the hydrophobic membrane.

3. The apparatus of claim 2, wherein the chamber comprises a tunnel or tube formed by the hydrophobic membrane.

4. The apparatus of claim 1, wherein the demulsifying portion comprises a funnel formed by the hydrophobic membrane.

5. The apparatus of claim 1, wherein the hydrophobic membrane is configured to filter the polymerized gel droplets.

6. The apparatus of claim 1, wherein the hydrophobic membrane has a pore size that is between 0.1 μm and 5 μm.

7. The apparatus of claim 1, wherein the demulsifying portion is configured to remove the oil from the polymerized gel droplets when the gel droplets contact the hydrophobic membrane.

8. The apparatus of claim 1, wherein the second channel is configured to form the polymerized gel droplets suspended in the oil, wherein the polymerized gel droplets have a diameter of between 50 μm and 500 μm.

9. The apparatus of claim 1, wherein the hydrophobic membrane is configured to remove at least 99% of the oil from the polymerized gel droplets.

10. A microfluidic apparatus comprising:
a component defining a first channel and a second channel, the first channel being configured to receive a dissociated tissue sample and an unpolymerized matrix material, and the second channel being configured to receive an oil and to intersect with the first channel such that the dissociated tissue sample, the unpolymerized matrix material, and the oil form polymerized gel droplets suspended in the oil; and
a demulsifying portion comprising a hydrophobic membrane in fluid communication with the component and configured to remove the oil from the polymerized gel droplets.

11. The apparatus of claim 10, wherein the demulsifying portion comprises a chamber at least partially formed by the hydrophobic membrane.

12. The apparatus of claim 11, wherein the chamber comprises a tunnel or tube formed by the hydrophobic membrane.

13. The apparatus of claim 10, wherein the demulsifying portion comprises a funnel formed by the hydrophobic membrane.

14. The apparatus of claim 10, wherein the hydrophobic membrane is configured to filter the polymerized gel droplets.

15. The apparatus of claim 10, wherein the hydrophobic membrane has a pore size that is between 0.1 μm and 5 μm.

16. The apparatus of claim 10, wherein the demulsifying portion is configured to remove the oil from the gel droplets when the polymerized gel droplets contact the hydrophobic membrane.

17. The apparatus of claim 10, wherein the second channel is configured to form the polymerized gel droplets suspended in the oil, wherein the polymerized gel droplets have a diameter of between 50 μm and 500 μm.

18. The apparatus of claim 10, wherein the hydrophobic membrane is configured to remove at least 99% of the oil from the polymerized gel droplets.

19. The microfluidic apparatus of claim 10, comprising an elution channel in fluid communication with the component and configured to elute the gel polymerized droplets from the demulsifying portion using an aqueous solution.

20. The microfluidic apparatus of claim 19, wherein the elution channel is configured to elute the polymerized gel droplets into a multi-well plate.

21. The microfluidic apparatus of claim 10, wherein the component defines one or more ports for receiving the dissociated tissue sample, the unpolymerized matrix material, the oil, or combinations thereof.

* * * * *